US008962289B2

(12) United States Patent
Albers et al.

(10) Patent No.: US 8,962,289 B2
(45) Date of Patent: Feb. 24, 2015

(54) STRAINS OF SACCHAROMYCES CEREVISIAE

(75) Inventors: Eva Albers, Partille (SE); Lisbeth Olsson, Göteborg (SE); Rakesh Koppram, Göteborg (SE)

(73) Assignee: Scandinavian Technology Group AB, Lund (SE)

( * ) Notice: Subject to any disclaimer, the term of this patent is extended or adjusted under 35 U.S.C. 154(b) by 0 days.

(21) Appl. No.: 13/885,037

(22) PCT Filed: Nov. 15, 2011

(86) PCT No.: PCT/SE2011/051368
§ 371 (c)(1),
(2), (4) Date: Jun. 5, 2013

(87) PCT Pub. No.: WO2012/067571
PCT Pub. Date: May 24, 2012

(65) Prior Publication Data
US 2013/0244247 A1 Sep. 19, 2013

(30) Foreign Application Priority Data
Nov. 15, 2010 (SE) ...................................... 1051194

(51) Int. Cl.
*C12N 1/12* (2006.01)
*C12P 7/06* (2006.01)
*C12P 7/10* (2006.01)
*C12R 1/865* (2006.01)
*C12N 9/04* (2006.01)
*C12N 15/01* (2006.01)
*C12N 15/81* (2006.01)
*C12Q 1/04* (2006.01)
*C12N 9/12* (2006.01)

(52) U.S. Cl.
CPC ... *C12P 7/06* (2013.01); *C12P 7/10* (2013.01); *C12R 1/865* (2013.01); *C12N 9/0006* (2013.01); *C12N 15/01* (2013.01); *C12N 15/81* (2013.01); *C12Q 1/04* (2013.01); *C12N 9/1205* (2013.01); *C12Y 101/01009* (2013.01); *C12Y 101/0101* (2013.01); *C12Y 101/01307* (2013.01); *C12Y 207/01017* (2013.01); *Y02E 50/16* (2013.01); *Y02E 50/17* (2013.01)
USPC .......................................... 435/161; 435/254.2

(58) Field of Classification Search
USPC .................... 435/252.3, 254.2, 161
See application file for complete search history.

(56) References Cited

U.S. PATENT DOCUMENTS 7,381,551 B2   6/2008   Wahlbom et al. .............. 435/161
7,531,348 B2   5/2009   Otero et al. .............. 435/254.21
2006/0110805 A1*  5/2006   Fotheringham et al. ...... 435/105
2009/0269797 A1   10/2009   Chen et al. ....................... 435/29
2010/0028975 A1*  2/2010   Gorwa-Grauslund ... 435/254.21
2013/0295620 A1   11/2013   Albers et al.

FOREIGN PATENT DOCUMENTS

WO         01/88094 A1    11/2001
WO         03/078642 A1    9/2003
WO       2004/085627 A1   10/2004
WO       2005/111214 A1   11/2005

OTHER PUBLICATIONS

Almeida, J., et al. (2009), "Screening of *Saccharomyces cerevisiae* strains with respect to anaerobic growth in non-detoxified lignocellulose hydrolysate", *Bioresource Technology*, 100: 3674-3677.
Fenge and Lüllau (2006), "Continuous culture", *Cell Culture Technology for Pharmaceutical and Cell-based Therapies*, 188-189.
Hawkins, R., et al. (1999), "Utilization of xylose for growth by the eukaryotic alga, *Chlorella*", *Current Microbiology*, 38: 360-363.
Martin, C., et al. (2007), "Adaptation of a recombinant xylose-utilizing *Saccharomyces cerevisiae* strain to a sugarcane bagasse hydrolysate with high content of fermentation inhibitors", *Bioresource Technology*, 98: 1767-1773.
Olofsson, K., et al. (2010), "Controlled feeding of cellulases improves conversion of xylose in simultaneous saccharification and co-fermentation for bioethanol production", *Journal of Biotechnology*, 145: 168-175.
Tomás-Pejó, E., et al. (2010), "Adaptation of the xylose fermenting yeast *Saccharomyces cerevisiae* F12 for improving ethanol production in different fed-batch SSF processes", *J ind Microbiol Biotechnol*, 37: 1211-1220.
Watanabe, T., et al. (2011), "A UV-induced mutant of *Pichia stipitis* with increased ethanol production from xylose and selection of a spontaneous mutant with increased ethanol tolerance" *Bioresource Technology*, 102: 1844-1848.
International Search Report and Written Opinion dated Mar. 2, 2012 issued in PCT/SE2011/051368.
International Search Report and Written Opinion dated Mar. 2, 2012 issued in PCT/SE2011/051369.

(Continued)

*Primary Examiner* — Maryam Monshipouri
(74) *Attorney, Agent, or Firm* — Harness, Dickey & Pierce, P.L.C.

(57) ABSTRACT

A method for producing a strain of *Saccharomyces cerevisiae* with introduced genes coding for xylose reductase, xylitol dehydrogenase and xylulokinase and with improved ethanol production, improved xylose conversion, reduced xylitol production and improved inhibitor tolerance is described. The method comprises culturing a strain of *Saccharomyces cerevisiae* at a continuous mode with a medium comprising essentially only xylose as carbon source at a temperature of 25-38° C., preferably 30-35° C., and an airflow of 0.040-0.055 vvm, and increasing the dilution rate to maintain a constant cell level, said cell level being in the range of 1.5-3.0 determined by optical density or equivalent analytical means, and adding at least one inhibitor to the cells and gradually increasing the addition of said inhibitor. Further, strains of *Saccharomyces cerevisiae* obtained by the method according to the invention are described.

9 Claims, 13 Drawing Sheets
(13 of 13 Drawing Sheet(s) Filed in Color)

(56) References Cited

OTHER PUBLICATIONS

International Preliminary Report on Patentability dated May 21, 2013 issued in PCT/SE2011/051368.

International Preliminary Report on Patenability dated May 21, 2013 issues in PCT/SE2011/051369.

International Search Report for PCT/SE2011/051368, ISA/SE, Stockholm, mailed Mar. 2, 2012.

C. Fredrik Wahlbom et al.: "Generation of the improved recombinant xylose-utilizing *Saccharomyces cerevisiae* TMB 3400 by random mutagenesis and physiological comparison with *Pichia stipitis* CBS 6054," FEMS Yeast Research, 2003, vol. 3, pp. 319-326.

Karin Öhgren et al.: "Simultaneous saccharification and co-fermentation of glucose and xylose in steam-pretreated corn stover at high fiber content with *Saccharomyces cerevisiae* TMB3400," Journal of Biotechnology, 2006, vol. 126, No. 4, pp. 488-498.

\* cited by examiner

Fig. 3 (continued)
Fig 3D
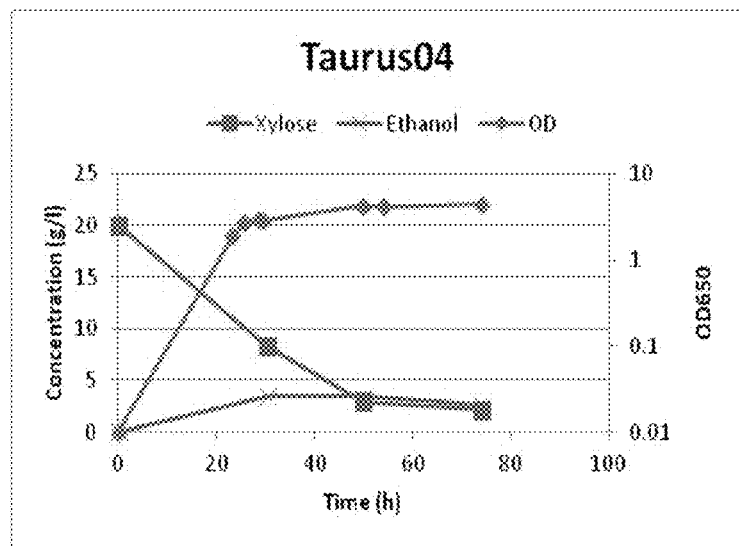
Fig 3E
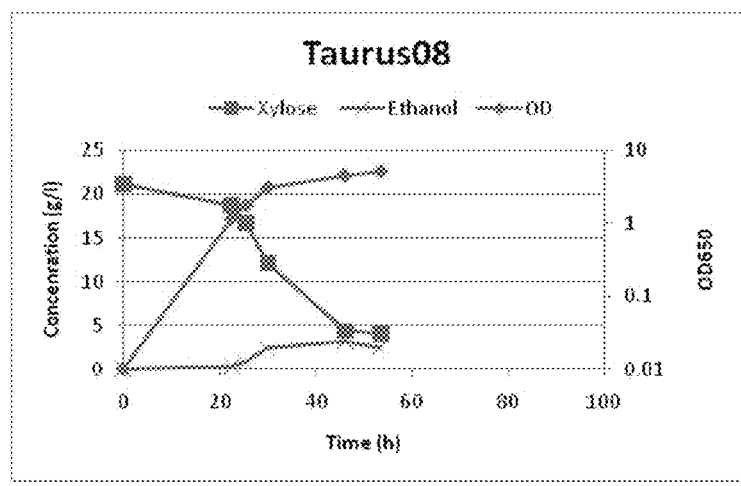
Fig 3F
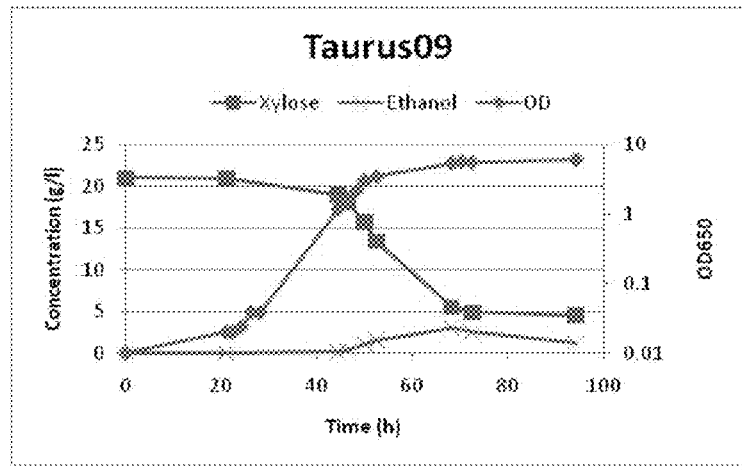

Fig. 3 (continued)
Fig 3G
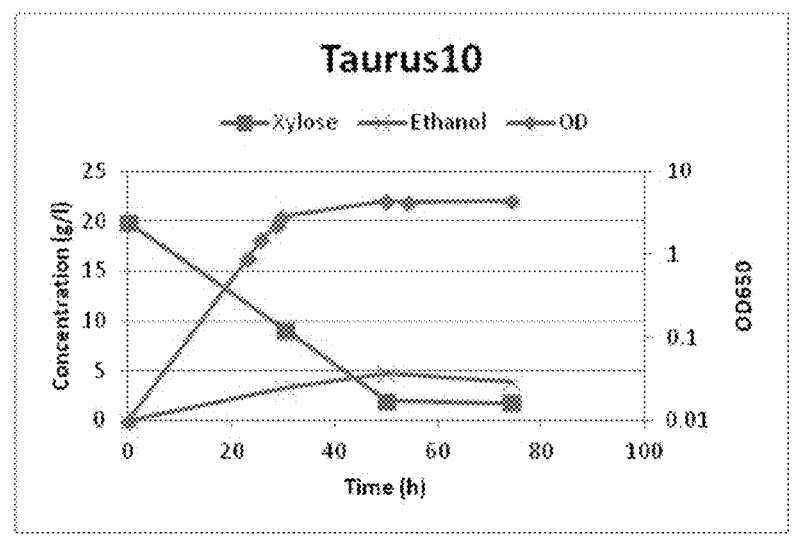
Fig 4A
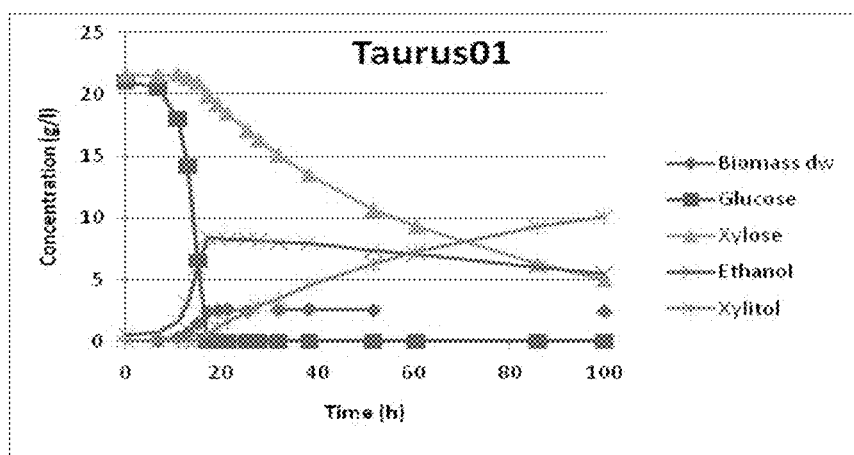

Fig. 4 (continued)
Fig 4B
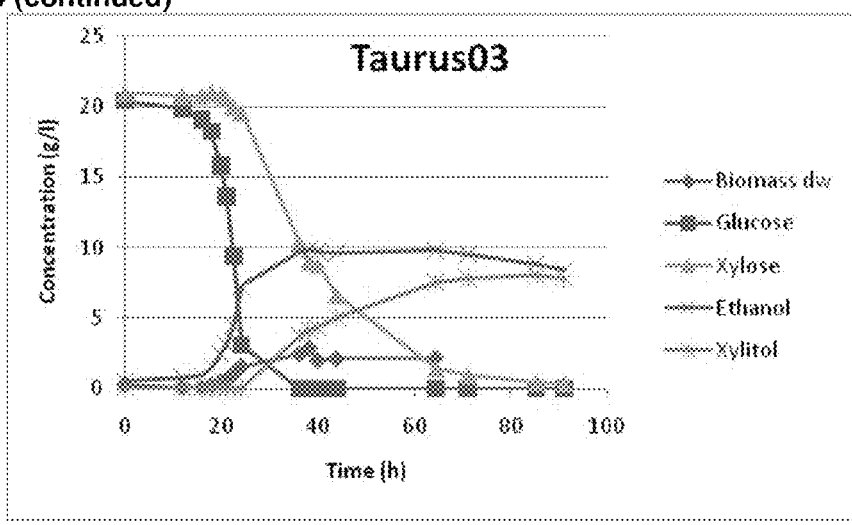
Fig 4C
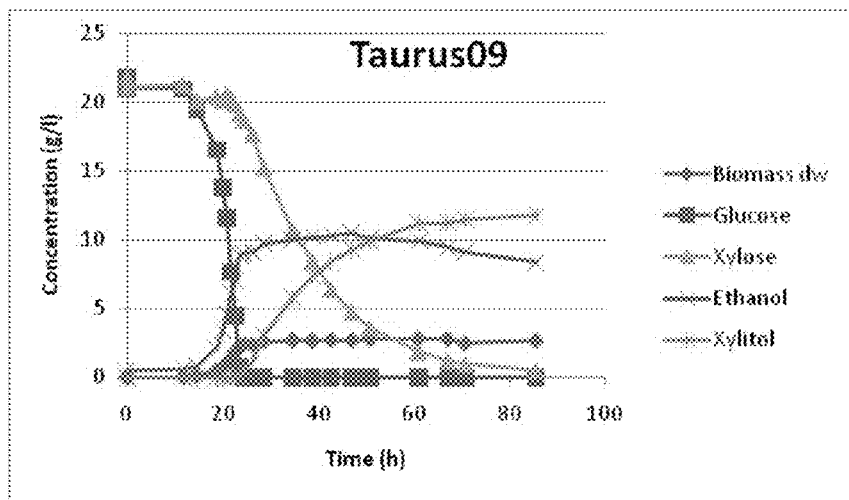
Fig 4D
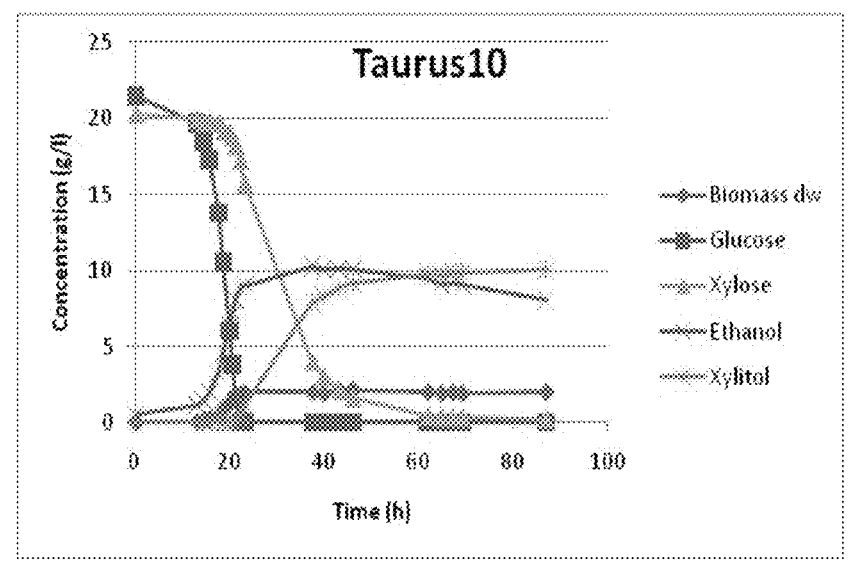

Fig. 6 (continued)
Fig 6B
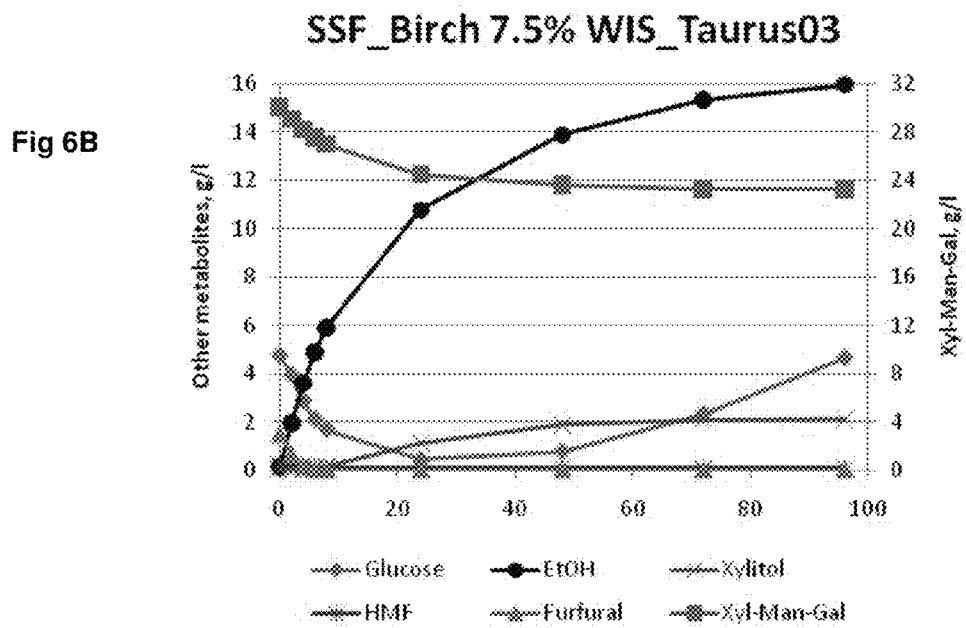
Fig. 7
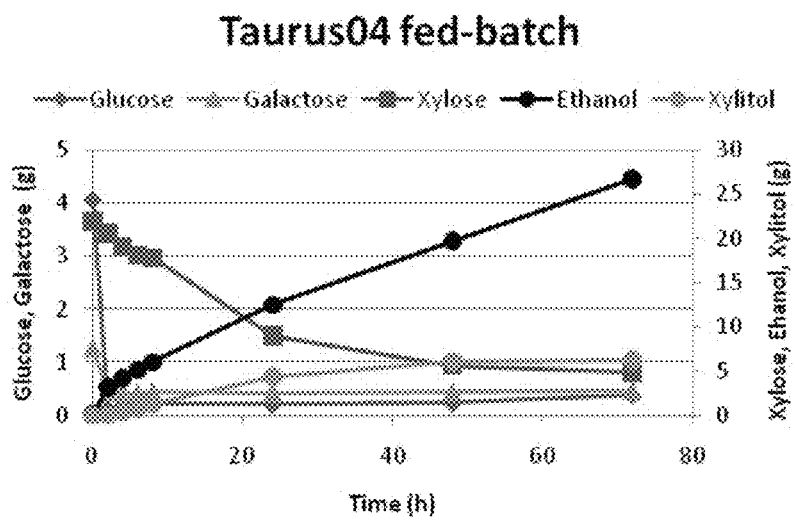

Fig. 13 (continued)
Fig 13B
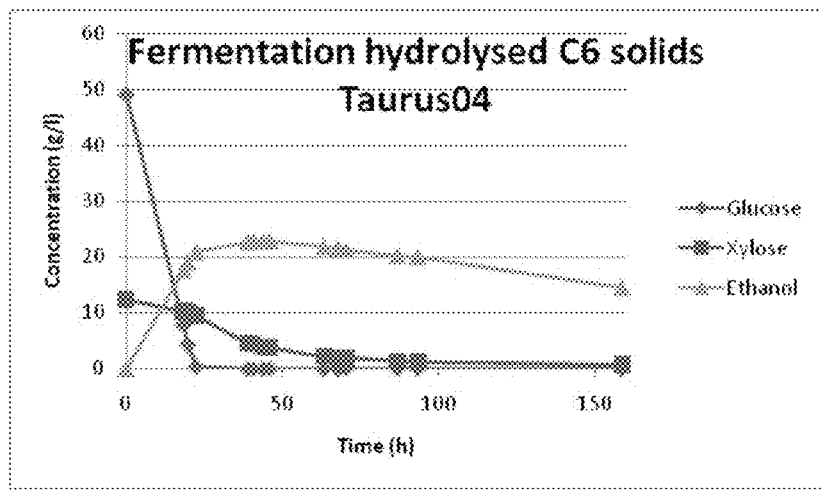
Fig 13C
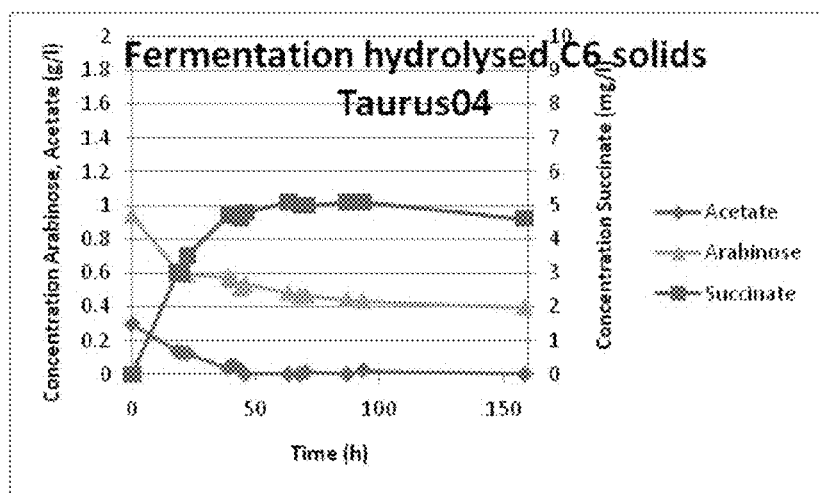

STRAINS OF *SACCHAROMYCES CEREVISIAE*

CROSS-REFERENCE TO RELATED APPLICATIONS

This application is a 371 U.S. National Stage of International Application No. PCT/SE2011/051368, filed Nov. 15, 2011. This application claims priority to Swedish Patent Application No. 1051194-7, filed Nov. 15, 2010. The disclosures of the above applications are incorporated herein by reference.

TECHNICAL FIELD OF THE INVENTION

The present invention relates to a method for producing a strain of *Saccharomyces cerevisiae* with introduced genes coding for xylose reductase, xylitol dehydrogenase and xylulokinase and with improved ethanol production, improved xylose conversion, reduced xylitol production as well as an improved inhibitor tolerance. The present invention further relates to strains of *Saccharomyces cerevisiae* obtainable by the method according to the present invention.

BACKGROUND ART

Environmental issues regarding the use of petrol as an automobile fuel and also the risk that todays oil wells in the future will run dry has led to an intense research regarding an alternative to the use of petrol. Ethanol has been found to be a good alternative to petrol since it to a large extent can be used instead of petrol without major changes of combustion engines. Ethanol can be used today to replace some of the fuel with very small or even without any adjustments at all to the engines.

Strains of the genus *Saccharomyces* are used widely in the industry for brewing, distilling, baking and various other applications. *Saccharomyces cerevisiae* is one of the most widely used microorganisms in industrial applications in view of it's ability to convert sugars such as glucose and sucrose to biomass, and fermenting these sugars to ethanol. Strains of *Saccharomyces cerevisiae* are used in the fuel industry in view of their ability to rather rapidly convert sugars into ethanol and since *Saccharomyces cerevisiae* has a better tolerance towards fermentation inhibitors and ethanol compared to bacteria and other yeast. WO2005/111214 discloses strains of *Saccharomyces cerevisiae* having an increased ability to produce ethanol in the presence of inhibitors such as furfural and 5-methoxy furfural.

Unlike bacteria and several yeast species, wild-type *Saccharomyces cerevisiae* is not able to use pentoses such as xylose and arabinose as carbon source. The ability of *Saccharomyces cerevisiae* to grow on abundant carbon sources such as side streams and waste material from other processes, such as agricultural waste material from e.g. maize and bagasse, and waste material from e.g. paper manufacture, is of great environmental, but also economical, value. Agricultural waste comprises a rather large fraction of hemicellulose, which contains many different sugar monomers. For instance, besides glucose, these sugar monomers can include xylose, mannose, galactose, rhamnose and arabinose. Xylose is the sugar monomer that is present in the largest amount and thus represents an important carbon source for the manufacturing of ethanol using yeasts, providing a huge economic and environmental advantage.

Genes encoding enzymes giving the ability to use xylose as carbon source have previously been introduced in *Saccharomyces cerevisiae*. EP 1 282 686 discloses recombinant *Saccharomyces cerevisiae* strains having incorporated genes for the enzymes xylose reductase, xylitol dehydrogenase and xylulokinase as well as having been subjected to a specific mutation. Said strains have the ability to ferment lignocellulose raw materials to ethanol. The strain deposited in Ep 1 282 686 is CBS 102679 (TMB3400, Taurus 01) and is generally recognised to be efficient in the prior art. The ethanol produced by the strain CBS 102679 has been considered very good compared to other prior art recombinant yeasts, but there is also a production of the undesirable byproduct xylitol. Therefore, there is still a need within the art to provide new strains of *Saccharomyces cerevisiae* having an even better ethanol production, better xylose conversion as well as lower xylitol production in view of the increasing environmental aspects of society today. Furthermore, it is desirable to provide strains having an even better inhibitor tolerance.

SUMMARY OF THE INVENTION

The aim of the present invention is therefore to solve the problems above and to provide novel strains of *Saccaromycese cerevisiae* having better xylose conversion, better ethanol production, lower production of the byproduct xylitol as well as an improved inhibitor tolerance, said strains of *Saccharomyces cerevisiae* having the ability to produce ethanol using essentially only xylose as carbon source.

According to a first aspect of the present invention this problem is solved using a method for producing a strain of *Saccharomyces cerevisiae* with introduced genes coding for xylose reductase, xylitol dehydrogenase and xylulokinase and with improved ethanol production, improved xylose conversion and reduced xylitol production, comprising the steps of:

a) culturing cells of *Saccharomyces cerevisiae* with introduced genes coding for xylose reductase, xylitol dehydrogenase and xylulokinase at a continuous mode with a medium comprising essentially only xylose as carbon source at a temperature of 25-38° C., preferably 30° C.-35° C., and an airflow of 0.01-0.06 vvm, and increasing the dilution rate to maintain a constant cell level, said cell level being in the range of 1.5-3.0 determined by optical density or equivalent analytical means, b) and adding at least one inhibitor to the cells and gradually increasing the addition of said inhibitor.

The important step is to maintain the cell level constant in the bioreactor. When improved cells have evolved, which can better utilize the substrate at the specific growth rate set by the dilution rate, more cells will be formed as a result of the improvement. This means that to keep the selection pressure an increase in growth rate is needed, which is obtained by increasing the dilution rate.

According to one embodiment of the present invention the medium of step a) comprises 15-25 g/l xylose, preferably about 20 g/l.

In a further embodiment the method further comprises the step of c) increasing the temperature to 35-45° C. and/or applying UV irradiation during the culturing, e.g. either after step a) or b).

An increase of temperature enriches the number of cells with a higher tolerance against stress.

The airflow used depends on the properties of the yeast strain that is used. In the case of a respiratory metabolism more air is required, e.g. in the case of xylose metabolism. As soon as ethanol production has begun less air is required and may be decreased in order to increase the selection pressure for the ethanol metabolism instead.

The xylose consumption capacity may be seen as composed of two components, the importing rate and at what concentration the import can be efficiently done, i.e. the affinity for xylose. The rate of import is tightly connected to the growth rate when xylose is the sole carbon source, i.e. how fast the xylose graph is decreased. The affinity for xylose is good if the xylose graph reaches close to zero, i.e. all of the xylose has been used.

For an efficient xylose conversion capacity additionally the carbon of xylose imported should be channeled to ethanol not to xylitol and as little as possible towards cell formation. The strains of the invention have both improved importing rate and affinity for xylose.

In another embodiment the improved ethanol production, improved xylose conversion and reduced xylitol production is in comparison to the strain deposited as CBS 102679 (TMB3400, Taurus 01). In another embodiment the cells as used in step a) of above method are cells of the strains as deposited CBS 102679. Said cells of *Saccharomyces cerevisiae* that are used as starting material in step a) have introduced genes for the enzymes xylose reductase, xylitol dehydrogenase and xylulokinase in order for the yeast to be able to ferment xylose. These genes can be obtained from any source from which such genes can be isolated. For instance can the genes coding for xylose reductase, xylitol dehydrogenase be obtained from *Pichia stipitis* and xylulokinase be obtained from *Saccharomyces cerevisiae*.

In one embodiment the method further comprises the step of d) selection of cells, from step b) or from step c), with xylose conversion ability and inhibitor tolerance.

According to another embodiment the selection is conducted on an agar plate with xylose as essentially sole carbon source and/or said at least one inhibitor or any other inhibitor. It is also possible that the selection is conducted on an agar plate with any carbon source and said at least one inhibitor or any other inhibitor. Thus, the strain may handle an environment with different types of inhibitors, not only the specific one used in the method of the invention for making the strain inhibitor tolerant.

To obtain an improved inhibitor tolerant xylose-fermenting yeast strain it is important to keep up both the selection pressure for xylose conversion and inhibitor tolerance. Since, glucose is a preferred carbon source of *Saccharomyces cerevisiae* the presence of this sugar inhibits the selection pressure for xylose. This was noted in some of the experiments in which the xylose conversion capacity was decreased while gaining inhibitor tolerance. Thus, most types of hydrolysates, that typically contain large amounts of glucose, can not be used in the method according to the invention. Thus, in order to produce a strain of the present invention, a laboratory medium (minimal or defined) should be provided, having xylose as essentially the sole carbon source, in the presence of inhibitors such as a synthetic mix or as a largely degraded hydrolysate, which are high in inhibitors and low in sugars, importantly the level of glucose and mannose should be very low.

In one embodiment of the present invention the inhibitor is chosen from furans such as HMF and furfural, organic acids such as acetic acid and formic acid and phenolic compounds. Further examples of inhibitors are given in the exemplary part of the present specification.

The present invention further relates to a strain of *Saccharomyces cerevisiae* with improved ethanol production, improved xylose conversion and reduced xylitol production, wherein said strain is Taurus03 with deposition number CBS128138.

In another embodiment the present invention also relates to a strain of *Saccharomyces cerevisiae* with improved ethanol production, improved xylose conversion and reduced xylitol production and improved inhibitor tolerance, wherein said strain is Taurus04 with deposition number CBS128139.

In one embodiment the present invention also relates to a strain of *Saccharomyces cerevisiae* with improved ethanol production, improved xylose conversion and reduced xylitol production and improved inhibitor tolerance, wherein said strain is Taurus07 with deposition number CBS128140.

All of the strains of the invention have been deposited at Centraalbureau voor Schimmelcultures (CBS), Uppsalalaan 8, 3584 CT Utrecht, the Netherlands.

*Saccharomyces cerevisiae* Taurus03 with deposit number CBS128138, has been deposited on $17^{th}$ of Oct. 2011.

*Saccharomyces cerevisiae* Taurus04 with deposit number CBS128139, *Saccharomyces cerevisiae* Taurus07 with deposit number CBS128140 have been deposited on $26^{th}$ of Oct. 2010. *Saccharomyces cerevisiae* Taurus 10 CBS 128141, which is also mentioned herein, has been deposited on 2 Nov. 2010.

Another embodiment of the invention is the use of a strain obtained by the inventive method for fermenting lignocellulose raw materials into ethanol. The lignocellulose raw material that is used can be any kind available. Examples are agricultural residues including corn stover and sugarcane bagasse, wood residues including sawmill and paper mill discards, and municipal paper waste.

Another embodiment of the invention is the use of a strain obtained by the inventive method in a simultaneous saccharification and fermentation (SSF) process.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will now be described in detail by examples with reference to the enclosed drawings.

FIG. 4: Glucose (squares) and xylose (triangles) consumption and formation of biomass (diamonds), ethanol (crosses) and xylitol (stars) in anaerobic bioreactor cultivations with minimal medium. Representative cultures shown of duplicates. FIG. 4*a* for Taurus 01, FIG. 4*b* for Tarurus 03, FIG. 4*c* for Taurus 09, FIG. 4*d* for Taurus 10.

FIG. 6: Concentration profiles of substrates, glucose (diamonds), xylose+mannose+galactose (squares, Xyl-Man-Gal), products, ethanol (circles), xylitol (crosses), and furan inhibitors, HMF (stars) and furfural (triangles) in SSF experiment on birch slurry at 7.5% WIS and 5 FPU/g WIS of cellulose degrading enzymes.

FIG. 7: Profiles of total amounts, glucose (diamonds), galactose (triangles), xylose (squares), ethanol (black circles) and xylitol (orange circles), in fed-batch fermentation of corn cobs liquor with Taurus04 and with the feed of glucose started after 2 h.

DETAILED DESCRIPTION OF PREFERRED EMBODIMENTS

Figure 1:
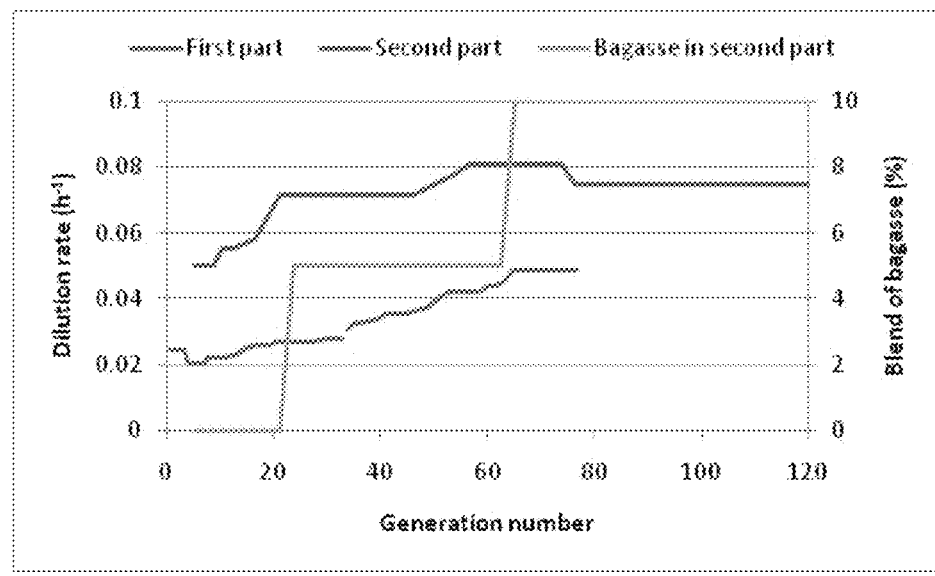
FIG. 1: Improvement in growth properties reflected by dilution rate during adaptation in continuous cultures with minimal medium described in example 1. In first part (blue line, starts at 0,025 dilution rate, $h^{-1}$) xylose was used as the only carbon source and in the second part (red line, starts at 0.05 dilution rate, $h^{-1}$) the temperature was increased to 35° C. and bagasse (green line, starts at 0 dilution rate, $h^{-1}$) blended into the medium at increased levels.

When conducting the experiments of the present invention conventional microbiological processes are used, unless otherwise indicated. Such processes are known to the skilled man in the art and are fully explained in the literature.

Further, all technical terms used in the present application have the meaning as is commonly understood by the skilled man.

The abundance of xylose in e.g. plant biomass and the possibility to use yeasts, such as *Saccharomyces cerevisiae*, to produce ethanol using xylose as carbon source has led to intense research within this field of technology. The conversion of xylose has however sometimes been poor resulting in a poor ethanol production. Further the production of the byproduct xylitol has been rather large.

The inventors of the present invention have in view of the above problems surprisingly developed improved strains of *Saccharomyces cerevisiae* with a more effective xylose conversion and as a result of that a better ethanol production. Further, a lower production of the byproduct xylitol has been observed. Furthermore, the improved strains have a better tolerance against inhibitors which are found in many lignocellulosic hydrolysates.

It should be noted that strains that are capable of using xylose as essentially sole carbon source are also able to grow on other sugars. The meaning of the phrase "essentially sole carbon source" means that trace amounts of other sugars also may be present. Glucose may be present and is usually converted first by *Saccharomyces cerevisiae* since it is a preferred sugar for yeast. Thereafter the xylose is used as the carbon source.

These desirable characteristics for *Saccharomyces cerevisiae* have been achieved using the already known strain of *Saccharomyces cerevisiae* known as XYLUSM125, TMB3400 or Taurus 01, having the deposit number CBS 102679. In this strain genes encoding enzymes giving the ability to use xylose as essentially the sole carbon source have already been introduced. As an alternative, other strains of *Saccharomyces cerevisiae* with the ability to use xylose as essentially sole carbon source can be used according to the present invention. The strains of the invention may be performed in industrial strains as well as laboratory strains even though industrial strains are preferred. An industrial strain is less well defined than the laboratory strains since it has several copies of each chromosome. Thus, manipulating industrial strains, as have been performed according to the present invention, is a larger challenge than manipulating laboratory strains.

The strains with improved ethanol production, improved xylose conversion and reduced xylitol production and improved inhibitor tolerance according to the present invention are obtained using non-recombinant methods. This means that recombinant DNA technology is not utilized to achieve strains with improved ethanol production, improved xylose conversion and reduced xylitol production and improved inhibitor tolerance. Recombinant DNA technology is, however, used to achieve e.g. the strain TMB3400 (Taurus01), which can be used as a starting material according to the present invention. Recombinant DNA techniques according to the present invention refer to techniques where genetic information is manipulated in vitro, while non-recombinant methods are not utilizing this manipulation in vitro.

According to the present invention, the desirable characteristics have been achieved in that mutations, normally occurring during growth and possibly elevated by UV irradiation, are selected and enriched during specific conditions in cultivations of *Saccharomyces cerevisiae*, i.e. directed evolution/adaptation or evolutionary engineering. The procedure of directed evolution can be divided into three steps: first allowing mutations to occur, thereafter selection of desirable traits by applying a selection pressure in culture, and finally screening/characterization of obtained strains to map properties.

Mutations arise during normal growth since some errors in the genetic code can occur during the replication process, in which the DNA is copied and transferred to the next generation. The probability for mutations to occur can be increased by certain chemicals or UV irradiation. The mutations may change properties of the cellular proteins such that the possibility for the organism to survive is increased or decreased.

The term "selection" refers to the process, the "adaptation", where cells with improved desired characteristics are enriched in the population. This is achieved by applying a selection pressure, which could be chosen from a large number of different conditions, in the cultivation by designing the growth conditions such that the desired properties are beneficial for the survival and performance of the microorganism. Selection pressure, as for the present invention, can be achieved by having xylose as essentially sole carbon source, having inhibitors present, or increasing the temperature. In addition, different selection pressures are achieved by the mode of cultivation. An increase in temperature may enrich cells with a higher general stress tolerance. It is very important to select and apply the proper selection pressure that allow the desired property to evolve. Certain selection pressures can be applied together in the same adaptation or in subsequent cultivations. Typically, according to the present invention, the cultivation can be performed in liquid medium or on agar plates. In liquid culture the proportion of improved cells is increased during the progress of the adaptation and is seen as an improvement in performance of the mixed population, as for the present invention reflected by improved ethanol production, improved xylose conversion and reduced xylitol production.

Importantly, the adaptation should proceed during many generations to allow suitable mutations to arise and enrich in the cell population. When performing the selection on agar plates, the cells are typically incubated during a time sufficient to allow cells having the ability to grow and form colonies. Larger colonies appearing on the agar plate are indicative of cells with an improved ability to grow at the applied condition as compared to smaller colonies showing an inferior ability.

In the present context the phrase "new generation" means, as is understood by a man skilled in the art, that a cell has been divided into two new cells and that the two new cells represent the new generation. In the present context the cells proceed to grow for many generations and until there cannot be observed any phenotypical changes anymore in the new generation compared to previous generations, i.e. phenotypical changes remain constant. Examples of phenotypical changes are for instance the maximal specific growth rate of the cells. This can be measured by measuring the optical density. Other phenotypical changes that can be observed are for instance the productivity of ethanol, the conversion of xylose and the production of the byproduct xylitol. There are no phenotypical changes observed anymore when these components are kept at a constant level.

Further, the term "screening" refers to a process where the performance of cells are characterised in a comparable way. The screening method should show the performance reflecting the desired properties of the cells and can be performed on agar plates or in liquid medium. Cells with improved desired characteristics can thus be identified and taken to a further characterization of other properties.

According to the present invention there is thus provided a method for producing a strain of *Saccharomyces cerevisiae* with introduced genes coding for xylose reductase, xylitol dehydrogenase and xylulokinase and with improved ethanol production, improved xylose conversion and reduced xylitol production an improved inhibitor tolerance.

Further, there are provided strains of *Saccharomyces cerevisiae* obtainable by the method according to the present invention.

Below follows examples for achieving the improved strains of *Saccharomyces cerevisiae* according to the present invention. All the work was started with the strain TMB3400 (Taurus 01), which previously has shown very good performance regarding xylose conversion capacity and rather low xylitol yields (Sonderegger, et al., 2006, Hahn-Hägerdal, et al., 2007). However, as stated previously, other strains of *Saccharomyces cerevisiae* may be used as long as it has the capacity to ferment xylose. By the present invention it has surprisingly been possible to produce even more efficient strains of *Saccaromyces cerevisiae* with regard to xylose conversion and ethanol production. A lower production of the byproduct xylitol has also been observed. Thus, the strains as obtained according to the present invention may be used in the fermentation of different lignocellulosic materials or waste materials from maize or bagasse comprising, in addition to glucose, considerable amounts of the sugar xylose. More efficient strains to be used in such fermentation processes will be of large economical and environmental value.

As will be seen in the experimental part, the strains of the invention have been shown to be superior compared to prior art strains regarding ethanol production, xylose consumption, xylitol production as well as inhibitor tolerance.

Example 1

Improvement of Xylose Conversion Capacity and Inhibitor and Temperature Tolerance Using Continuous Cultures The directed adaptation series was started with strain Taurus01 and performed in continuous cultures in a bioreactor (approx. 750 ml working volume of 1 l, Belach Bioteknik AB, Sweden) with minimal medium (Verduyn, et al., 1992) with 2 times higher trace metal solution than used according to Verduyn and 0.1 ml/l of PEG P2000 as antifoam (in bioreactor cultivations). The pH was controlled at 5.0 with 2M NaOH and stirrer speed was set at 350 rpm. For starting the culture a 50 ml inoculum with 20 g/l xylose and 20 g/l glucose (in 250 ml baffled shake flask, incubated for 24-36 h, 30° C., shaking 180 rpm) was added to the bioreactor (with minimal medium and 20 g/l xylose and 20 g/l glucose, total volume 800 ml, no gas inflow). The culture was run for 15-20 h before the continuous mode was started with inflowing medium having only 20 g/l xylose as carbon source and an overflow tube determining the outflow. The precise culture volume was determined at the end of the culture and was 740-780 ml. The optical density at 650 nm (OD) was measured every working day as a measure of the cell density. Samples for measurement of extracellular metabolites (also from the medium flask) and aliquots of cells to be saved frozen (1 ml of cell suspension were added to 0.5 ml sterile 60% glycerol, stored at −80° C.) were taking regularly. HPLC (Dionex, Ultimatum 3000, RI detection at 35° C., UV detection at 210 nm, columns at 45° C. from BioRad; AminexHPX-87H and 30×4.6 mm Cation-H micro-guard, eluent 5 mM $H_2SO_4$ at a flow of 0.6 ml/min) were used to determine metabolites. Contamination of the culture was regularly checked, ocularly using a microscope, not to be present.

The first part of the adaptation was run at 30° C. and airflow of 35 ml/min. The intention was to keep the OD at a value 2-2.5. An increase in the OD level is an indication for improvement of growth properties and thus the flow rate could be increased to apply a higher selection pressure. Correspondingly, if an decrease in the OD level was seen the selection pressure was too high and accordingly the flow rate is needed to be decreased. Thus, the increase in flow rate (or recalculated to dilution rate) is a measure of the increased performance of the cells. After 15 generations the temperature in the reactor was increased to 35-45° C. for 24 h and cells were recovered from the culture by both saving a frozen aliquot and streaking a sample on a xylose agar plate (20 g/l xylose, 20 g/l peptone, 10 g/l yeast extract and 20 g/l agar). A strain that was obtained after such temperature treatment was named Taurus02. Cells from the agar plate were used to start a new continuous culture. The culture was run for 77 generations during which an increase in the dilution rate was seen (FIG. 1) and the final strain was named Taurus03. This strain thus belongs to the first generation of xylose strains.

The second part of the adaptation series was run at an airflow of 13 ml/min and additional selection pressures were applied. First, the temperature in the bioreactor was increased to 35° C. (both for batch and continuous phases) and secondly a toxic bagasse was blended in to the medium at increased levels. This bagasse hydrolysate was prepared (at SEKAB E-technology, Sweden) using a pre-treatment (with 2% $SO_2$, ~190° C.) which was run to long (residence time 13-15 min) resulting in a somewhat degraded hydrolysate with low levels of sugars (4 g/l glucose, 5 g/l xylose, 0.4 g/l galactose) and high inhibitor content. The pH of the hydrolysate for the aliquot to be used was adjusted to 5.0 with 5M NaOH at the time of each medium preparation. The culture was first run for 21 generations on only xylose minimal medium to allow the cells to adapt to the higher temperature. The culture was then in total run for 120 generations. An increase in dilution rate were seen during the progress of the culture, but when increasing the content of the bagasse in the medium the growth was slower and the dilution rate were consequently needed to be decreased (FIG. 1). However, as the generations proceeded at a certain bagasse content an improvement in dilution rate was seen (FIG. 1).

At the end of the directed evolution regime the second generation of xylose strains was obtained and further characterised. The third last strain was named Taurus04 and the two last strains, which were named Taurus05 and Taurus06, were used to select special inhibitor tolerant clones of the heterogeneous cell population obtained during adaptation. Samples of the cells were diluted in a ten times dilution series with sterile water. 10 μl of each dilution were dropped on an agar plate (20 g/l glucose, 20 g/l peptone, 10 g/l yeast extract, 20 g/l agar) with a synthetic mixture of 12 selected inhibitors. The inhibitors were present at concentrations of 2.5 g/l hydroxymethylfurfural, 0.82 g/l furfural, 4.7 g/l acetic acid, 0.9 g/l formic acid, 1.8 g/l levulinic acid, 0.10 g/l vanillin, 0.03 g/l coniferyl aldehyde, 0.75 mg/l cinnamic acid, 15 mg/l hydroquinone, 82 mg/l syringaldehyde, 15 mg/l 4-hydroxybenzoic acid, and 15 mg/l 4-hydroxy-3-methoxyphenyl acetone (guaiacyl acetone). The plates were incubated until some larger colonies were seen. Cells from these colonies (Taurus05 one colony, Taurus06 3-4 colonies) were restreaked on bagasse plates (50% toxic bagasse, 20 g/l glucose, 20 g/l peptone, 10 g/l yeast extract, 20 g/l agar) and incubated two days at 30° C. and four days at room temperature. Several of the larger colonies were restreaked on new bagasse plates and incubated for another 2+4 days. From these plates the six largest colonies for each strain were separately streaked on xylose minimal medium plates. After incubation at 30° C. for seven days the 9-10 largest colonies of each strain were used to start small cultures (10 ml in 50 ml falcon tube) in rich xylose medium (20 g/l xylose, 20 g/l peptone, 10 g/l yeast extract) which was grown overnight and subsequently used for preparing the frozen stock of cells, resulting in the strains named Taurus07 and Taurus08.

Example 2

Figure 2:
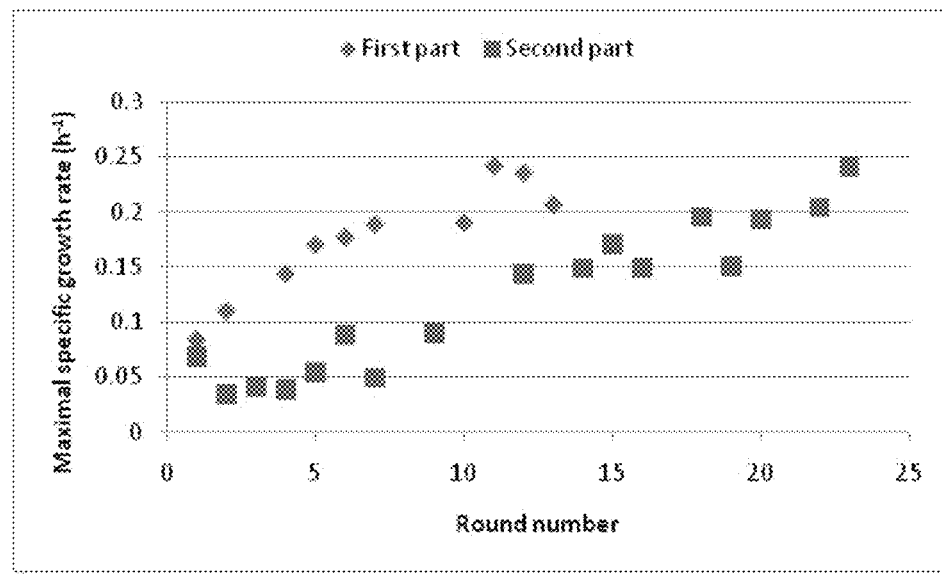
FIG. 2: Improvement in maximal specific growth rate during adaptation in repetitive shake flask cultures with minimal medium described in example 2. First part (diamonds) with 20 g/l xylose and second part (squares) with 5 g/l. In the second part from round 10 series D is shown.

Improvement of Xylose Conversion Capacity Using Repetitive Shake Flask Cultures The Taurus02 strain, which is developed from TMB3400 (Taurus01) was used as the starting strain for a directed adaptation scheme using repetitive batch cultures. The cultivations were done in shake flask cultures at 30° C. with an agitation of 180 rpm in 100 ml flasks with 50 ml of minimal xylose medium (Verduyn, et al., 1992) with pH 5.5 and 2 times higher trace metal solution than used according to Verduyn. The first part of the adaptation scheme was done with 20 g/l xylose in the medium. Each culture was run until the optical density at 650 nm (OD) reached a value of 1.8-3 when growth started to cease and then an aliquot of cells were transferred to the flask of next round with fresh medium to give a start OD of 0.07. In round 7, the performance was improved to such a degree that the start OD was decreased to 0.06 for round 8, 0.05 for rounds 9-10 and approx 0.02 for rounds 11-13. In total, 13 cultivations were done allowing 73 generations during the adaptation regime and cells from 7 of the rounds were saved frozen (1 ml of cell suspension were added to 0.5 ml sterile 60% glycerol, stored at −80° C.). The cultures were followed by measuring OD and from these calculating the maximal specific growth rate (FIG. 2) and by measuring extracellular metabolites for each culture at the start and at the transfer to next round. HPLC (Dionex, Ultimatum 3000, RI detection at 35° C., UV detection at 210 nm, columns at 45° C. from BioRad; AminexHPX-87H and 30×4.6 mm Cation-H micro-guard, eluent 5 mM $H_2SO_4$ at a flow of 0.6 ml/min) were used to determine metabolites and these results showed that the xylose level at the transfer was quite high, approx 12-16 g/l, and thus the adaptation was taken to the next part. The last strain was named Taurus09 and is thus another first generation xylose strain together with Taurus03. This strain had an improved maximal specific growth rate about three times at adaptation conditions (FIG. 2).

The xylose concentration in the second part of the adaptation was selected as 5 g/l, based on the poor performance of strain Taurus 09 in medium with 5 g/l of xylose as compared to 10 g/l both done in separate cultivations. In this adaptation the transfer of cells was done at OD 2.8-3 and the start OD was 0.1 (except for the first four rounds when start OD of 0.01 was used) and OD and metabolites were followed as before. The adaptation proceeded during 9 rounds corresponding to 47 generations. Because of the limited improvement in specific growth rate seen at this point (FIG. 2) the culture was divided into four parts. Two parts were illuminated with UV light to increase the number of mutations and two parts were transferred to the next round without any treatment. For the UV treatment agar plates with minimal xylose medium was used and cells were spread across 4 agar plates which was dried. Two plates were exposed to UV light, using a TFM-26V, P/N 95-0422-02, 25 Watt High Performance UV transilluminator from Ultra-Violet Products Ltd. with a wavelength of 302 nm, set on High Intensity, for 60 seconds and two for 90 seconds. Cells were immediately collected from the plates and used to start up new cultures in the adaptation series. Cells exposed both for 60 and 90 seconds were used together in a new shake flask culture. UV-treated and not treated cells were both used to start cultures at normal conditions and oxygen limited conditions, see table.

| Series name | A | B | C | D |
|---|---|---|---|---|
| Type of condition | Aerobic, untreated cells | Aerobic, UV treated cells | Limited $O_2$, UV treated cells | Limited $O_2$, untreated cells |

The oxygen limited conditions were achieved by using a special shake flask. This limited oxygen flask was constructed from a 250 ml shake flask with baffles and two arms. An air filter (filter 21978 from INFORS HT) was connected to one of the arms and a rubber tubing with a syringe in the outer end was connected to the other arm for sampling. All openings were sealed with parafilm. These adaptation series were followed for 14-15 rounds, except for series B where cells died in the second round. The number of generations achieved during this last part was 83 for series A, 68 for series C, and 89 for series D. Cells were regularly saved frozen (prepared as described above) during the proceeding of the adaptation. The last strain of series D showed the best performance and was selected as a second generation xylose strain and named Taurus10. This strain had an improved maximal specific growth rate by about 5 times at the low xylose levels in the adaptation (FIG. 2).

Example 3

Characterization of Strains Regarding Xylose Fermentation Capacity at Different Conditions a) Shake Flask Cultures with Minimal Medium and Xylose as Only Carbon Source The first type of characterisation applied was shake flask cultures with minimal medium and only xylose as carbon source. The cultivations were performed in 50 ml medium in 100 ml flasks and started by adding cells from a frozen stock to obtain an OD of 0.01. The cultures were incubated at 30° C. and 180 rpm, which results in semiaerobic conditions in the flasks, and the cells and metabolite concentrations were followed.

Strains on which this type of characterisation was conducted:

Taurus02
Taurus03
Taurus07
Taurus08
Taurus09
Taurus10

Figure 3A:
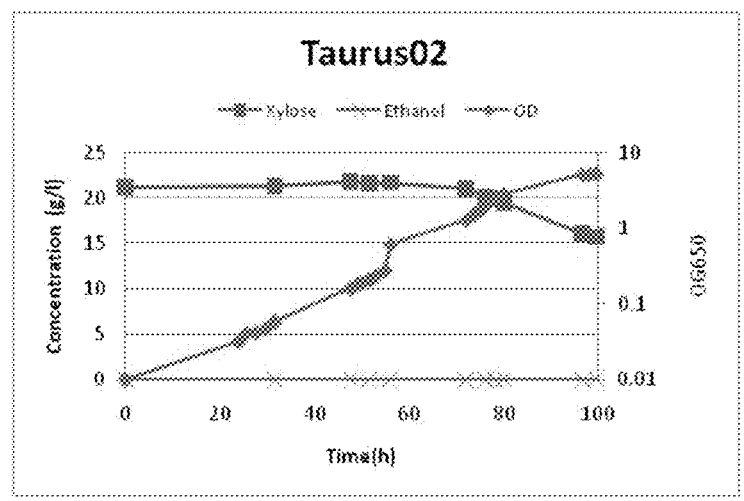
FIG. 3*a* for Taurus 02, FIG. 3*b* for Tarurus 03, FIG. 3*c* for Taurus 07, FIG. 3*d* for Taurus 04, FIG. 3*e* for Taurus 08, FIG. 3*f* for Taurus 09, FIG. 3*g* for Taurus 10.
Figure 3B:
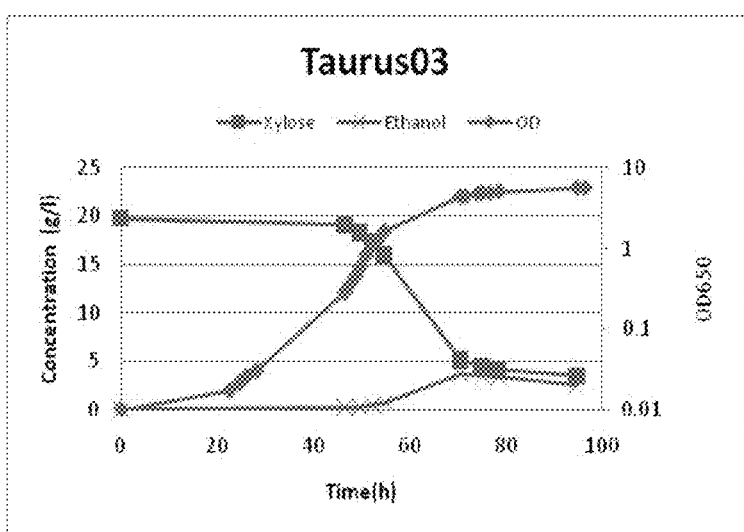
FIG. 3: Xylose consumption (squares) and ethanol (crosses) and cell (diamonds) formation in shake flask cultures with minimal medium and xylose as the sole carbon source. Cell concentration are estimated as optical density at 650 nm (OD).
Figure 3C:
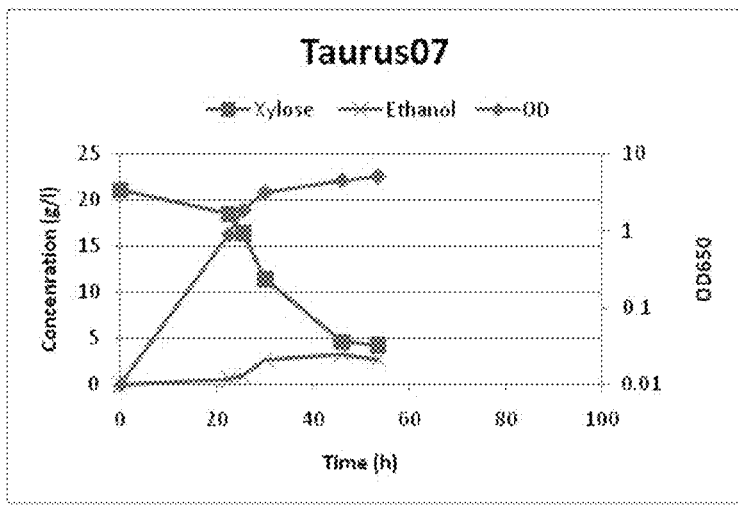

A faster maximal specific growth rate was achieved already for the first generation of xylose strains from both types of directed evolution schemes, Taurus03 and Taurus09, and was only marginally improved for the second generation of xylose strains (Table 1, FIG. 3). The strains have shifted types of metabolism towards ethanol production and consequently less cells were formed. Thus, it can be concluded that the xylose fermentation was more efficient also taken into account that all the improved strains could use a larger portion of the xylose. The best strains in this respect Taurus10 could use more than 90% of the xylose and consequently this strain produced the highest ethanol level 4.2 g/l. No difference in xylose fermentation was seen between the inhibitor tolerant strains Taurus07 and Taurus08.

TABLE 1

Growth rates, yields, residual levels of xylose and maximal ethanol concentrations during shake flask cultivations with minimal medium and xylose as sole carbon source. Taurus02, 07, 10 was done in duplicate cultures, Taurus03 in triplicates and the results from these are given as a range.

| Strain | Maximal specific growth rate ($h^{-1}$) | Ethanol yield (g/g consumed xylose) | Biomass (OD/g/l consumed xylose) | Xylose residual level (g/l) | Maximal ethanol concentration (g/l) |
|---|---|---|---|---|---|
| Taurus02 | 0.06-0.09 | 0-0.06 | 0.9-1.2 | 16-18 | 0-0.2 |
| Taurus03 | 0.19-0.22 | 0.22-0.32 | 0.28-0.34 | 3.1-4.0 | 3.4-4.0 |
| Taurus04 | 0.23 | 0.29 | 0.24 | 2.1 | 3.5 |
| Taurus07 | 0.22-0.24 | 0.16-0.20 | 0.28-0.31 | 4.3-5.2 | 3.2-3.3 |
| Taurus08 | 0.21 | 0.19 | 0.30 | 4.0 | 3.2 |
| Taurus09 | 0.21 | 0.18 | 0.37 | 4.5 | 3.0 |
| Taurus10 | 0.19-0.20 | 0.22-0.26 | 0.26-0.28 | 1.8-2.0 | 4.2-4.7 |

Xylitol was for all strains formed at low levels (<0.06 g/g xylose consumed)

b) Anaerobic Bioreactor Cultures with Mineral Medium and Glucose and Xylose as Carbon Sources In an industrial setting the anaerobic performance is very important and thus characterisation in such type of cultures was performed. Since anaerobically, cells cannot grow solely on xylose as carbon source (FIG. 4), a mixture of glucose and xylose were used.

Pre-cultures were prepared by adding 100 μl of frozen cells from stock culture to 100 ml of minimal media containing 20 g/l glucose and 20 g/l xylose. The culture was then incubated aerobically at 30° C. for 48 h before inoculation of the bioreactors. The medium in the bioreactor for anaerobic cultivations was complemented with 0.1 ml/l antifoam (Polypropylenglykol P2000), 10 mg/l ergosterol and 0.42 g/l Tween 80. Bioreactors with a working volume of two liters were used (Belach Bioteknik AB, Sweden) and anaerobic conditions was achieved by flushing nitrogen gas through the fermentor at 0.4 l/min. The temperature was controlled at 30° C., the pH at 5.0 with 2 M NaOH, and the stirrer speed at 500 rpm. Cells from the pre-culture were then added to reach a starting $OD_{650}$ of 0.01 in the bioreactor. Both OD and dry cell weight were measured and extracellular metabolite samples were collected regularly during the course of the fermentation. Duplicate cultures of each strain were done, which gave very similar results.

Strains on which this type of characterisation was conducted:

Taurus01
Taurus03
Taurus09
Taurus10

Also during anaerobic condition the xylose fermentation was more efficient for all the improved strains (Table 2, FIG. 4). It was seen both as an increased rate of xylose consumption and all xylose could be consumed by the improved strains. Especially, the strain Taurus10 showed a fast consumption. Accompanied with the improved ethanol formation by our strains also a reduced formation of the by-product xylitol was seen. For Taurus03 the reduction in the xylitol yield was as much as 40%.

TABLE 2

Yields and xylose consumption in anaerobic cultivations on minimal medium with xylose and glucose as carbon sources. The maximal deviation of duplicate cultures is given.

| Strain | Yields | | | Xylose consumed at 70 h (% of initial) | Maximal ethanol concentration (g/l) |
|---|---|---|---|---|---|
| | Ethanol (g/g consumed sugars) | Xylitol (g/g consumed xylose) | Biomass (g/g consumed sugars) | | |
| Taurus01 | 0.34 ± 1% | 0.61 ± 1% | 0.11 ± 2% | 62 ± 0.5 | 8.4 ± 0.1 |
| Taurus03 | 0.28 ± 1% | 0.38 ± 0.5% | 0.08 ± 6% | 94 ± 0.5 | 10.0 ± 0.2 |
| Taurus09 | 0.28 ± 3% | 0.57 ± 0.5% | 0.08 ± 3% | 95 ± 0 | 10.3 ± 0.2 |
| Taurus10 | 0.24 ± 1% | 0.50 ± 0.4% | 0.07 ± 1% | 98 ± 0 | 10.1 ± 0.0 |

The strains of the invention (Taurus 03, 09 and 10) had a higher ethanol concentration as well as lower xylitol production compared to well known Taurus 01.

c) Anaerobic Fermentation of Corn Cobs Liquor in Shake Flask Cultures

For the next step in the characterisation the performance in real industrial substates was evaluated by investigated the fermentation in corn cob hydrolysate. Corn cobs were pre-treated by dilute acid added as $SO_2$, and made by SEKAB E-technology, Sweden. The pre-treated slurry was filtered to obtain the liquor part.

In the pre-culture cells were grown on minimal media with glucose and xylose as described under b, after 24 h some corn cobs liquor was supplemented to the shake flasks and left for incubation another 18 h. Cells were harvested by centrifugation. For fermentation corncobs liquor supplemented with 0.5 g/l $(NH_4)_2HPO_4$ was used as media and pH was set to 6.0. Cells harvested (by centrifugation) from the pre-culture were added to give an approximate starting cell density at 3 g dry weight/l. Incubation of the cultures was done with 50 ml of medium in 100 ml shake flasks at 30° C. and 180 rpm and anaerobic conditions were obtained by using air plugs filled with glycerol. Samples for metabolites were taken after 0, 2, 4, 6, 8, 24, 48, 72 and 96 h. Strains on which this type of characterisation was conducted:

Taurus03
Taurus04
Taurus09
Taurus10

Figure 5:
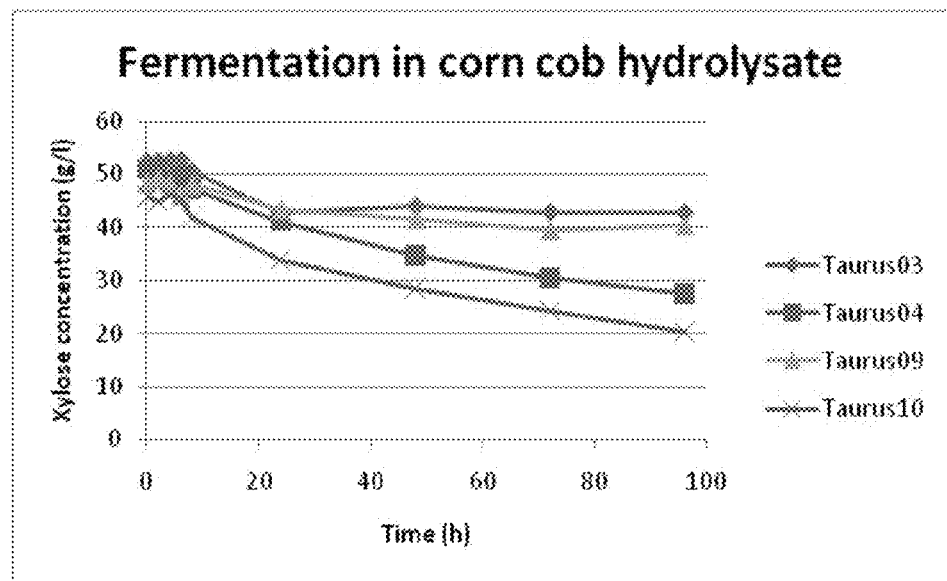
FIG. 5: Xylose consumption in anaerobic shake flask cultures with corn cob liquor by first generation of xylose strains, Taurus03 (diamonds) and Taurus09 (triangles), compared to second generation xylose strains evolved from these, Taurus04 (squares) and Taurus10 (crosses), respectively.

The data in Table 3 and FIG. 5 clearly show that the second generation xylose strains, Taurus04 and Taurus10, gave a higher final ethanol concentration and xylose conversion after 96 h compared to their respective parental strains, Taurus03 and Taurus09. In spite of the large xylose conversion, the yield of the by-product, xylitol, is kept at a low level, (FIG. 5).

TABLE 3

Yields of products, xylose consumption, and final ethanol levels in anaerobic shake flask cultures on corncobs liquor. Single cultivations were done.

| Strain | Ethanol yield (g/g consumed sugars) | Final EtOH conc. after 96 h (g/l) | Xylose consumed after 96 h (%) | Xylitol yield (g/g consumed xylose) |
|---|---|---|---|---|
| Taurus03 | 0.46 | 9.81 | 18.66 | 0.17 |
| Taurus04 | 0.41 | 14.52 | 46.03 | 0.13 |
| Taurus09 | 0.51 | 9.46 | 16.65 | 0.47 |
| Taurus10 | 0.42 | 15.76 | 55.45 | 0.21 | d) SSF (Simultaneous Saccharification and Fermentation) Experiments on Corn Cob and Birch Slurries Another typical process for ethanol production is the SSF process. In this process the hydrolytic enzymes are added together with yeast to achieve a simultaneous break down of the cellulose in the pre-treated slurry and fermentation of monomeric sugars. In the process substrate and process steps have been used to resemble as much as possible an industrial situation. Cell propagation was done in aerated fed-batch culture. The pre-culture for the propagation was done in 50 ml of minimal medium (pH 6.0) with 20 g/l glucose and 20 g/l xylose in 150 ml shake flasks. The pre-culture was started with a small portion; 100 μl of freezed cells and run in a rotary shaker at 30° C. for optimally 24 h (18-36 h). The medium (500 ml) in the batch contained 50 g/l molasses with 23.5 g/l $(NH_4)_2SO_4$, 3.0 g/l $KH_2PO_4$, 2.25 g/l $MgSO_4.7H_2O$ and 99 μg/l biotin, 360 ppm Vitahop (hop extract to suppress bacteria) and 1.2 ml/l antifoam (silicon based, Nopcomaster ENA-309, Nopco Paper Technology AB). The whole pre-culture were added to start the cultivation (in Labfors bioreactor, Infors AS), which was run with aeration at 1 vvm, adjustment of pH to 5.0 with 3 M NaOH, and stirring speed at 700. The batch was run until the sugar was finished (approx. 8-10 h) and then the feed was started. The feed contained hydrolysate of the material used in the forthcoming SSF (pH adjusted to 5, diluted corresponding to 7.5% WIS) and molasses was included giving a total hexose sugars concentration of 75 g/l. When the fed-batch phase started the stirrer speed was increased to 1000 rpm and the aeration increased to 1.0 vvm based on final volume. The feeding was added at a constant rate of 0.1 $h^{-1}$ and run for 20 h giving the final volume of 1.5 l. Cells were harvested by centrifugation (8 min at 1800×g) and resuspended in sterile 0.9% NaCl. The SSF part (total medium 1.5 kg) were run on slurry of pre-treated lignocellulosic material (pH 5.0, adjusted with NaOH) at 7.5% WIS and supplemented with 0.5 g/l $(NH_4)_2HPO_4$, 125 ppm Vitahop and 0.4 ml/l antifoam (same as in propagation). Cells resuspended in 0.9% NaCl were added to give an initial cell concentration of 3 g dry weight/l and enzymes (NS-22074 or Cellic C-tec2, Novozymes) were added at to give 5 FPU/g WIS to start the process. The fermenter (without baffles, Labfors) was controlled at 35° C., pH adjustment with 3 M NaOH to 5.0, stirrer speed at approx. 300-400 rpm and all inlets were closed and the outlet through condenser was open. Samples for metabolite analysis were taken at least at: 0, 2, 4, 6, 8, 24, 48, 72, and 96 h.

Strains on which this type of characterisation was conducted:

Taurus01
Taurus03
Taurus04
Taurus10

Figure 6A:
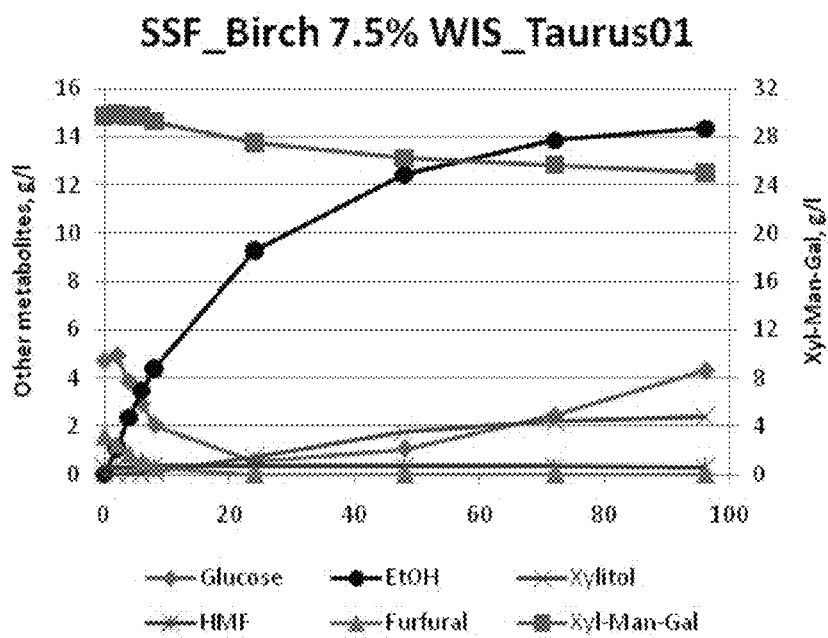
FIG. 6a for Taurus 01 and 6b for Taurus 03.

In the SSF processes on 7.5% WIS of corn cob slurry (the full slurry described in part c) it was as well clearly seen that the improved xylose consumption capacity of the strains of the invention were seen also in such a process (Table 4). Furthermore, the by-product formation of xylitol was reduced as also seen in the other types of characterisations (FIG. 6).

TABLE 4

Xylose consumption and xylitol formation in SSF experiments on corn cob slurry at 7.5% WIS and 5 FPU/g WIS of cellulose degrading enzymes. Duplicate cultures were performed and followed for 96 h.

| Strain | Xylose consumption (% of initial) | Xylitol formation (weight-% of consumed xylose) |
|---|---|---|
| Taurus01 | 31 ± 3 | 55 ± 5 |
| Taurus03 | 46 ± 6 | 39 ± 0 |
| Taurus04 | 43 ± 5 | 49 ± 1 |
| Taurus10 | 56 ± 4 | 37 ± 1 |

SSF characterisation was also performed using another type of material, birch, which is a high xylose containing lignocellulosic material. Wood chips of birch were pre-treated by dilute acid (~1% $SO_2$, 190° C., and residence time of 5 min, done at SEKAB E-technology). The pre-treated slurry were run at 7.5% WIS and also with this material the improved xylose consumption was seen (FIG. 6).

e) Fed-batch fermentation of corn-cobs Since the xylose consumption is under glucose repression (see also FIG. 4, xylose consumption starts after glucose depletion) another setup for the fermentation of hydrolysate was designed. The corn cob liquor (described in part c) was used in a fermentation and after glucose depletion a feed of glucose was started.

Cells were produced in the same manner as for a SSF process described above. The cells were loaded into 800 ml of concentrated medium consisting of corn cob liquor and nutrients as for a SSF process. The concentrations of corn cob liquor, nutrients, and cells at the end of the fed-batch corresponds to a similar SSF process. In the experiment the corn cob liquor was diluted to correspond to a WIS content of 7.5%. Cells were added and after 2 h glucose solution was started to be fed into the reactor at 5.53 ml/h during the rest of the cultivation. Samples for metabolites were taken after 0, 2, 4, 6, 8, 24, 48, and 72 h.

Strain on which this type of characterisation was conducted:

Taurus04

This setup was very successful, almost all xylose was consumed (FIG. 7) and more than 25 g ethanol was formed during 72 h and the production had not ceased at this point.

f) Test of Inhibitor Tolerance on Agar Plates

The strains from the second part of the directed evolution scheme using continuous cultures were adapted to increase their inhibitor tolerance. Thus, the inhibitor tolerance of these strains were evaluated using plate assays. A sample of cells from the frozen samples were diluted with sterile distilled water to yield an OD of 1. From this dilution a ten times dilutions series was made using distilled water and 10 µl of each dilution was dropped on a YPD (rich medium, yeast extract, peptone, glucose) agar plate with the inhibitor mixture of 12 compounds described above in example 1. The plates were incubated at least 2 days at 30° C. to allow the cells to grow and to be clearly seen.

Strains on which this type of characterisation was conducted:

Taurus03, Taurus04, Taurus05, Taurus06

Figure 8:
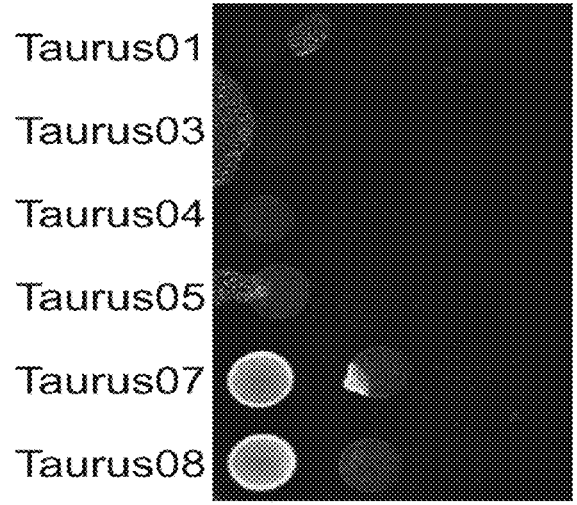
FIG. 8: Serial dilution series tested on YPD agar plate with mixture of 12 inhibitors. Each circle corresponds to one dilution and the more diluted to the right.

As seen in FIG. 8 the adapted strains displayed a better growth in the more diluted samples (column 2) compared to the parental strain Taurus03.

g) Anaerobic Fermentation of Bagasse Hydrolysate in Shake Flask Cultures

The performance in real industrial substrates was also investigated in fermentation with bagasse hydrolysate.

For the pre-culture, 100 µl of frozen cells from stock culture were added to 100 ml of minimal media with 20 g/l glucose and 20 g/l xylose. The culture was incubated aerobically at 30° C. and after 24 h some bagasse hydrolysate was supplemented to the shake flasks and left for incubation another 6.5 h. Cells were harvested by centrifugation. For fermentation tests different concentration of bagasse hydrolysate (20%, 50% and 75%) were supplemented with yeast extract (10 g/l) and pH was set to 6.0. Cells harvested from the pre-culture were added to give an approximate starting cell density at 3 g dry weight/l. Fermentation tests were performed with 50 ml of medium in 100 ml shake flasks at 30° C. and 180 rpm and anaerobic conditions were obtained by using air plugs filled with glycerol. OD from fermentation with 20% hydrolysate was followed along the process and measured al 650 nm.

Strains on which this type of characterisation was conducted:

Taurus03, Taurus04, Taurus07, Taurus10

Figure 9:
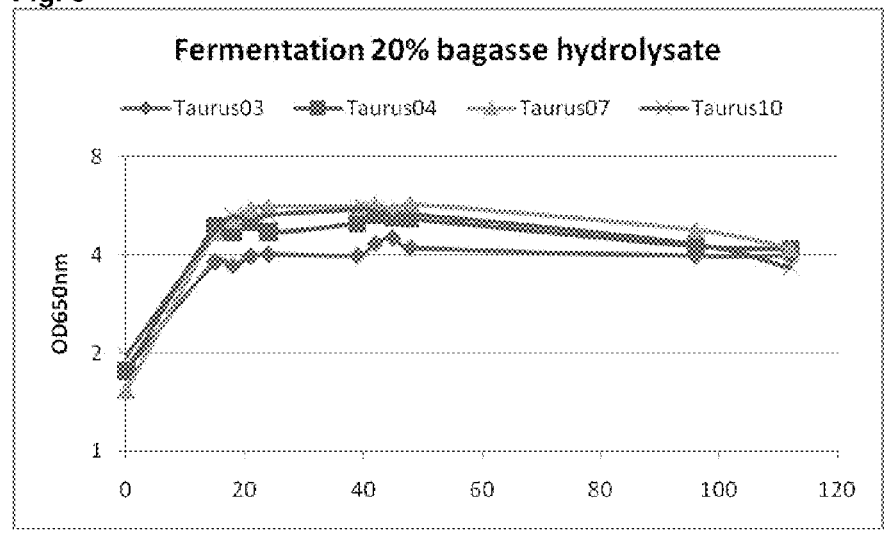
FIG. 9: Anaerobic fermentation of bagasse hydrolysate in shake flask cultures with *S. cerevisiae* Taurus 03, 04, 07 and 10.

Table 5, 6 and 7 as well as FIG. 9 show that the second generation xylose strains, Taurus04 and Taurus07, grew faster and gave higher ethanol yield, higher xylose conversion and less xylitol formation compared to their parental strains Taurus03. Furthermore, Taurus10 obtained from parental strain Taurus09 was also compared. In spite of the large xylose conversion, the yield of the by-product, xylitol, was kept at a low level in all cases. When hydrolysate was diluted to 20% xylose conversion was in all cases higher than 99%, see FIG. 9.

TABLE 5

Ethanol yield, xylose consumption and final ethanol concentration in anaerobic shake flask cultures on 20% bagasse hydrolysate. Single cultivations were done.

| Strain | Ethanol yield (g/g consumed sugars) | Final EtOH conc. after 112 h (g/l) | Xylose consumed after 112 h (%) | Xylitol yield (g/g consumed xylose) |
|---|---|---|---|---|
| Taurus03 | 0.37 | 16.84 | 99.28 | 0.22 |
| Taurus04 | 0.42 | 22.86 | 99.62 | 0.19 |
| Taurus07 | 0.38 | 16.78 | 99.67 | 0.17 |
| Taurus10 | 0.36 | 15.78 | 99.58 | 0.27 |

TABLE 6

Ethanol yield, xylose consumption and final ethanol concentration in anaerobic shake flask cultures on 50% bagasse hydrolysate. Single cultivations were done.

| Strain | Ethanol yield (g/g consumed sugars) | Final EtOH conc. after 136 h (g/l) | Xylose consumed after 136 h (%) | Xylitol yield (g/g consumed xylose) |
|---|---|---|---|---|
| Taurus03 | 0.37 | 15.54 | 95.84 | 0.20 |
| Taurus04 | 0.40 | 16.31 | 98.79 | 0.15 |
| Taurus07 | 0.41 | 17.15 | 99.86 | 0.14 |
| Taurus10 | 0.40 | 16.25 | 98.46 | 0.24 |

TABLE 7

Ethanol yield, xylose consumption and final ethanol concentration in anaerobic shake flask cultures on 75% bagasse hydrolysate. Single cultivations were done.

| Strain | Ethanol yield (g/g consumed sugars) | Final EtOH conc. after 136 h (g/l) | Xylose consumed after 136 h (%) | Xylitol yield (g/g consumed xylose) |
|---|---|---|---|---|
| Taurus03 | 0.44 | 12.28 | 75.33 | 0.18 |
| Taurus04 | 0.44 | 13.55 | 83.28 | 0.17 |
| Taurus07 | 0.45 | 14.02 | 86.46 | 0.12 |
| Taurus10 | 0.43 | 12.71 | 81.07 | 0.25 | h) SSF (Simultaneous Saccharification and Fermentation) Experiments on Wheat Straw Slurry Another typical process for ethanol production is the SSF process. In this process the hydrolytic enzymes are added together with yeast to achieve a simultaneous break down of the cellulose in the pre-treated slurry and fermentation of monomeric sugars. In the process substrate and process steps were used to resemble as much as possible an industrial situation. Cell propagation was done in aerated fed-batch culture. The pre-culture for the propagation was done in 50 ml of minimal medium (pH 6.0) with 20 g/l glucose and 20 g/l xylose in 150 ml shake flasks. The pre-culture was started with a small portion; 100 µl of freezed cells and run in a rotary shaker at 30° C. for optimally 24 h (18-36 h). The medium (500 ml) in the batch contained 50 g/l molasses with 23.5 g/l $(NH_4)_2SO_4$, 3.0 g/l $KH_2PO_4$, 2.25 g/l $MgSO_4.7H_2O$ and 99 µg/l biotin, 360 ppm Vitahop (hop extract to suppress bacteria) and 1.2 ml/l antifoam (silicon based, Nopcomaster ENA-309, Nopco Paper Technology AB). The whole pre-culture were added to start the cultivation (in Labfors bioreactor, Infors AS), which was run with aeration at 1 vvm, adjustment of pH to 5.0 with 3 M NaOH, and stirring speed at 700. The batch was run until the sugar was finished (approx. 8-10 h) and then the feed was started. The feed contained hydrolysate of the material used in the forthcoming SSF (pH adjusted to 5, diluted corresponding to 5% WIS) and molasses were included giving a total hexose sugars concentration of 75 g/l. When the fed-batch phase started the stirrer speed was increased to 1000 rpm and the aeration increased to 1.0 vvm based on final volume. The feeding was added at a constant rate of 0.1 h$^{-1}$ and run for 20 h giving the final volume of 1.5 l. Cells were harvested by centrifugation (8 min at 1800×g) and resuspended in sterile 0.9% NaCl.

The SSF part (total medium 1.5 kg) were run on slurry of pre-treated lignocellulosic material (pH 5.0, adjusted with 3 M NaOH) at 5% WIS and supplemented with 0.5 g/l $(NH_4)_2HPO_4$, 125 ppm Vitahop and 0.4 ml/l antifoam (same as in propagation). Cells resuspended in 0.9% NaCl were added to give an initial cell concentration of 3 g dry weight/l and enzymes (Cellic C-tec2, Novozymes) were added at to give 10 FPU/g WIS to start the process. The fermenter (without baffles, Labfors) was controlled at 35° C., pH adjustment with 3 M NaOH to 5.0, stirrer speed at approx. 300-400 rpm and all inlets were closed and the outlet through condenser was open. Samples for metabolite analysis were taken at least at: 0, 2, 4, 6, 8, 24, 48, 72, 96 and 137 h.

Strains on which this type of characterisation was conducted:

Taurus07

Figure 10:
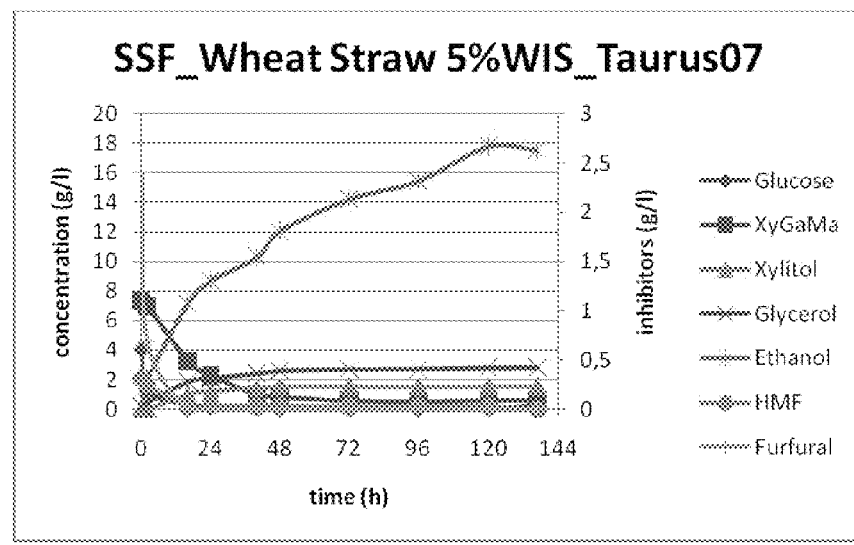
FIG. 10: SSF (simultaneous saccharification and fermentation) experiments with Taurus 07 on wheat straw slurry.

In the SSF process on 5% WIS of wheat straw slurry it was as well clearly seen that the improved xylose consumption capacity of the strains of the invention were seen also in such a process. Furthermore, the by-product formation of xylitol was reduced as also seen in the other types of characterisations, see FIG. 10.

TABLE 8

Percentage of soluble xylose consumption and xylitol formation in SSF experiments wheat straw slurries at 5% WIS and 10 FPU/g WIS of cellulose degrading enzymes.

| Strain | Soluble xylose consumed after 137 h | Xylitol formation | Final ethanol concentration | Ethanol yield (g/g glucose and xylose in the medium) |
|---|---|---|---|---|
| Taurus07 | 91.21% | 1.54 | 17.54 | 0.41 | i) Evaluation and Fermentation with *Saccharomyces Cerevisiae* Strain, Taurus 04, in an Industrial Demo Scale Fermentation Plant Yeast Culture The yeast culture Taurus 04 was propagated in three steps with increasing culture volume. The yeast was propagated in the third step in a culture tank of 10 m³. The propagation was done fed-batch with a molasses based medium. Th propagation provided yeast biomass in an enough amount to be used in the SSF process and the hydrolysate fermentation described below.

The yield from the propagation step was 0.25 g/g during batch and 0.36 g/g during fed-batch. The ethanol concentration was 0 g/l during the entire propagation, which is optimal from a fermentation perspective. If ethanol is found in the medium the yield of yeast cells decreases, which is undesirable. Thus, the yeast Taurus 04 is propagated well in a large scale.

Pre-Treatment of Corncob

The raw-material was corncob residues provided from Hungary. The material had a dry weight of about 85%. The raw-material was pre-treated with dilute sulphuric acid as catalyst at the process parameters shown below in order to provide a slurry.

| Catalyst | Acid concentration, % | Temperature, ° C. | Pressure, bar | Time, min |
|---|---|---|---|---|
| Period 1 | $H_2SO_4$ | 0.58 | 184 | 11.2 | 4.9 |
| Period 2 | $H_2SO_4$ | 0.58 | 186 | 11.5 | 5.0 |

In both of the experiments less than 200 kg filtrate/slurry was added at start. Initially, also water and yeast slurry were added to each fermentor. Some further chemicals were also added, which are shown below together with the process parameters.

| | |
|---|---|
| Temperature, ° C. | 35 |
| pH | 5.5 |
| $NH_3$ | 3 |
| $H_3PO_4$ | 1 |
| Foam inhibitor, L | 2 |
| VitaHop S, L | 0.5 |
| Initial amount filtrate/slurry, kg | 200 |

In the first experiment (hydrolysate fermentation) the slurry was filtrated and only the liquid fraction was used. 2840 litre filtrate and about 1144 litre additional liquid was totally added during the experiment. The filtrate was continuously added during the first 24 h of the experiment.

Enzymes corresponding to 5.3 FPU/g WIS (water insoluble solids) were added initially to hydrolyse oligomeric carbohydrates. The yeast concentration was about 5 g/l (calculated on the dry weight, DS).

Figure 11A:
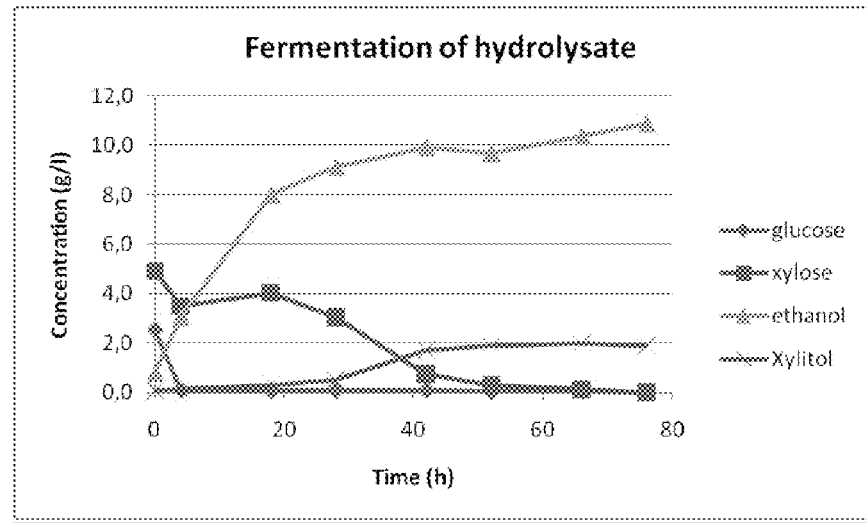
FIG. 11: Fermentation with *S. Cerevisae* strain, Taurus 04, in an industrial demo scale fermentation plant in the hydrolysate of corn cob residual slurry (FIG. 11a) and in a corn cob residual slurry in combination with a SSF process (FIG. 11b).

Results: A complete consumption of xylose is observed. 10% of the xylose is converted to lactic acid and xylitol and the remaining 90% of the xylose have been converted to ethanol. The final concentration of ethanol is 10.9 g/l, see FIG. 11a.

The inhibitors HMF and furfural had been detoxified by the yeast and these concentrations are at 0 g/l throughout the experiment. It is also observed that both glucose and xylose have been consumed at the same rate as the feeding of slurry during the first 24 h and that the ethanol produced thereafter must originate from xylose since the hexoses already are consumed.

In the second experiment (the SSF process) the entire slurry was added. 2844 kg slurry and 1092 litre liquid were added. In addition, enzyme corresponding to an enzyme activity of 15 FPU/g WIS was also added. The yeast concentration was 5.0 g/l (TS).

Figure 11B:
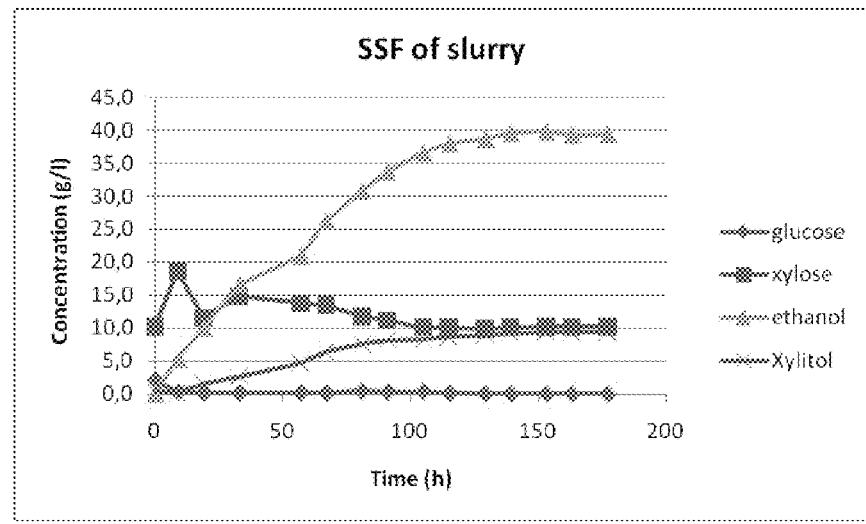

Results: In the second experiment the concentration of glucose and mannose is close to 0 g/l during the entire experiment as well as the concentration of lactic acid. The yeast consumes the xylose steadily to about 100 h. An effective fermentation of both hexoses and xylose leads to a final concentration of ethanol of 39.4 g/l, which corresponds to a conversion of xylose to ethanol of about 40%, see FIG. 11b.

j) Tolerance to Acetate and HMF during Growth on Xylose by Strains Taurus01, 03, 04, 07, 09 and 10

Experimental Details:

Xylose media at either 50 or 100 g/l and pH 5.0 was prepared containing 10 g/l yeast extract, 100 mM potassium phthalate with acetate and HMF at different levels. Acetate was added as sodium acetate yielding a level of acetic acid at 0, 4, 7, or 10 g/l (zero, low, medium and high). HMF were added at 0, 2, or 5 g/l (zero, low and high). All compounds were dissolved in some amount of water, pH was adjusted before dilution to final volume and the solution was filter-sterilised. The pH was measured on the sterile media and ranged between 4.94-5.15. All combinations result in 24 different types of media. The media was labeled as 1-12 for 50 g/l of xylose and 13-24 for 100 g/l of xylose. The acetate levels was put in groups of three or 1-3, 4-6, 7-9, 10-12 for zero, low, medium and high levels respectively (and corresponding for high xylose). Within each group of three the HMF level was increased from zero to low and high (e.g. 1, 2, 3). The above can be seen in FIG. 10. However, the figure does not show the situation when there is no concentration of either HMF or acetate. Furthermore, the graphs for test 11 and 12 are not shown in FIG. 10 due to a too toxic environment for the strains.

Inoculum cultures were done with YPDX medium and grown for approx. 24 h. Cells were harvested by centrifugation and resuspended in sterile mQ water. The biomass concentration was determined and a cell suspension at approx. 3 g dry weight/l was prepared by dilution with sterile mQ water.

The fermentations were done in triplicates with 170 µl of media and 30 µl of cell suspension giving a starting cell concentration at 0.46 g dry weight/l in the BioScreen (Growth Curves OY, Finland) at 30° C. for 72 h with continuous shaking. The condition of the BioScreen is semiaerobic. At the end of cultivation, the media from the triplicate cultures were mixed and filtered for HPLC analysis (on BioRad HPX87H column) for determination of fermentation products, HMF, acetate, and xylose.

Figure 12:
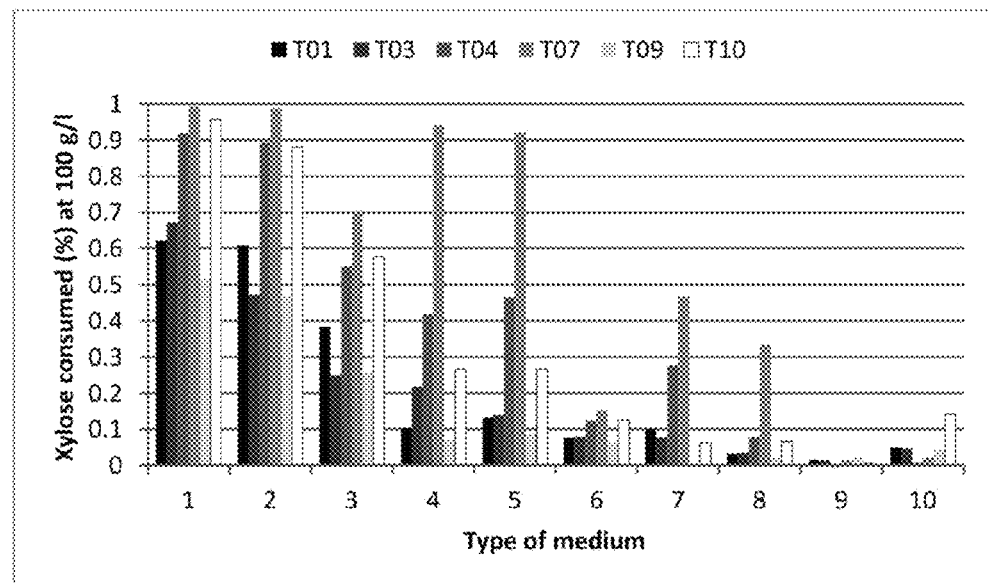
FIG. 12: Tolerance to acetate and HMF at different concentrations during growth on xylose by strains Taurus, 01, 03, 04, 07, 09 and 10.

Results:

The xylose consumption, ethanol production and growth properties was determined and the strain Taurus07 showed better performance at more challenging conditions with higher HMF levels and higher acetate levels, see FIG. 12

High xylose levels impose extra stress for the cell that have problems at higher HMF levels.

k) Fermentation on C5 Material with the Taurus04 Strain

The C5 liquor was diluted to a xylose concentration of 50-60 g/L. Dilution was done based on the xylose concentration in the liquor. pH was adjusted of the liquor to 5.5 (with KOH). The liquor was dispensed into 125 mL Erlenmeyer flasks with 60 mL liquor per flask. Antibiotic (penicillin G or virginiamycin) was added at 5 ppm to prevent bacterial contamination. Urea was added at 0.06 g/L (1 mM) and yeast extract at 0.5 g/L (for nutrition). Yeast was inoculated at 0.5 g dry yeast/L. The flasks were incubated at 32° C. (in shaking water bath at 125 rpm).

Figure 13A:
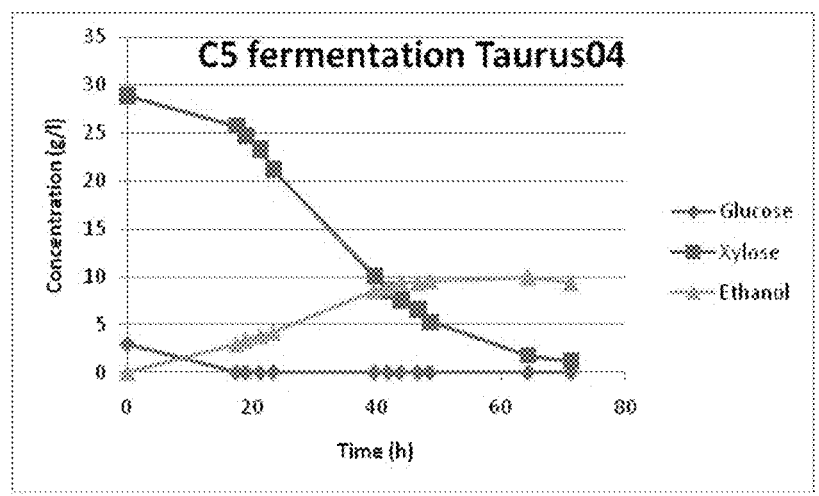
FIG. 13: Sugar consumption in C5 fermentation with Taurus 04, FIG. 13a, consumption/production profiles in fermentation of hydrolysed C6 solids with Taurus 04, FIG. 13b, and consumption/production profiles in fermentation of hydrolysed C6 solids with Taurus 04, FIG. 13c.

The xylose was consumed efficiently, less than 20% xylose remained after 48 h. Ethanol was produced during most part of the fermentation reaching 10.1 g/l as the maximum level after 64 h. This gives an ethanol yield of 0.34 g ethanol/g consumed sugars (from start to 64 h). The ethanol yield during only the xylose phase, i.e. from time 17 h to 64 h, was 0.30 g ethanol/g consumed xylos, see FIG. 13a.

l) Fermentation of Hydrolysed C6 Solids with Taurus 04

For initial adaptation of the cells in the inoculum, 30 ml of centrifuged and sterile filtered C6 hydrolysate was added to the culture (in the same way as for the C5 fermentation, 5 h incubation time). As for the C5 fermentation the pH was adjusted with 10 M KOH and the urea and yeast extract was dissolved in the pH adjusted hydrolysate to dilute the hydrolysate as little as possible (remaining particles after the hydrolysis was not taken away). The starting cell concentration in the main culture was 0.5 g dry weight/l.

The sugars were consumed efficiently. All glucose was finished after less than 24 h and after another 48 h more than 85% of the xylose was consumed. Ethanol was mainly produced during the initial 48 h reaching 22.8 g/l as the maximum level after 46 h. This gives an ethanol yield of 0.39 g ethanol/g consumed sugars (from start to 46 h). The ethanol yield during only the xylose phase, i.e. from time 22 h to 46 h, was 0.34 g ethanol/g consumed xylose, see FIG. 13b.

m) Simultaneous Saccharification and Fermentation of C5 Material and C6 Solids with Taurus 04 Strain The cell propagation was performed as fed-batch cultivation in YP medium with 20 g/l glucose and 20 g/l xylose. The feed consisted of C5 liquor adjusted to pH 5.0 with 5 M KOH and 40 g/l of sucrose supplemented. Cells were harvested by centrifugation and resuspended in water.

The medium for the SSF experiment was prepared at final volume of 1500 g of slurry with 15% total C6 solids. Since the C6 material contained 30% solids and 70% moisture, 750 g of C6 material were mixed with 750 g of C5 fraction and pH was adjusted to 5.5 with 10M KOH. Since the levels of xylose and acetic acid in the material was too low to represent appropriate conditions, 64.5 g xylose and 3 g acetic acid were dissolved in the slurry to yield total concentrations of approx 57 g/l and 4 g/l, respectively. Urea was added at 0.06 g/l, penicillin at 5 ppm, and antifoam (Polyethylen glycol) at 0.2 ml/l. The conditions of the SSF cultivation in Labfors fermenter (Infors HT) were: temperature 32° C., pH controlled at 5.5 with 5 M NaOH, stirrer speed at 600 rpm, and closed gas inlet. The cultivation was started by adding cells to give 1 g dry weight/l and 50 mg crude extract/g cellulose of Cellic Ctec2 enzymes (Novozymes). The cultivation was followed for 120 h by sampling of extracellular medium (centrifuged at 14 500 rpm, 2 min, before filtered and analysed as described above).

Figure 14:
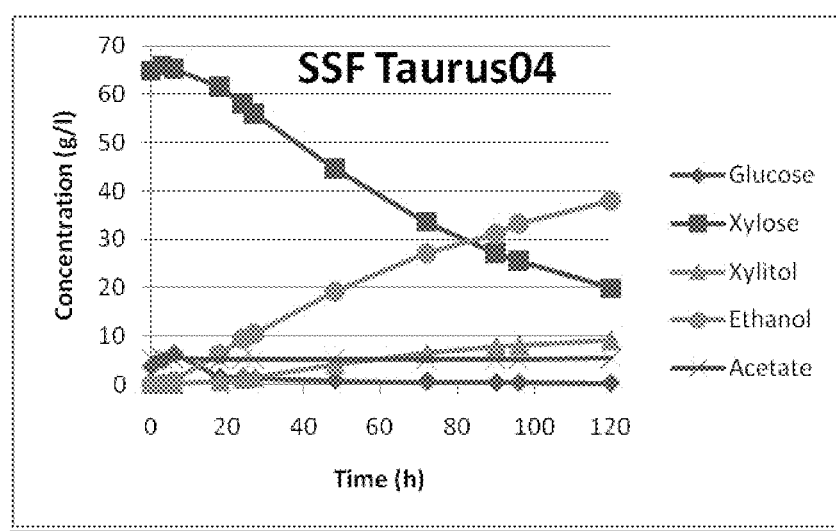
FIG. 14 Simultaneous saccharification and fermentation of C5 material and C6 solids with Taurus 04 strain

As shown in FIG. 14, 20 g/l of xylose remained after 120 h of process which corresponds to that 70% of the solubilized xylose was consumed by the yeast. The xylitol concentration at the end of fermentation was 9 g/l and thus some of the xylose was not converted to ethanol. Glucose was slightly increased during the first 6 h of process owing to the action of cellulolytic enzymes, but no glucose accumulation was found later in the process. This fact suggests that the yeast is consuming glucose well and enzymatic hydrolysis could be a limiting factor. Final ethanol concentration was 38.1 g/l. From the initial loading of 15% total solids, 228.75 g of total sugars were potentially available in 1.5 l of slurry. Thus, the ethanol produced corresponds to a yield of 48% of the theoretical yield based on total available sugars, FIG. 14.

The invention claimed is:

1. A strain of *Saccharomyces cerevisiae*, wherein said strain is Taurus 03 with deposition number CBS128138.

2. A strain of *Saccharomyces cerevisiae*, wherein said strain is Taurus 04 with deposition number CBS128139.

3. A strain of *Saccharomyces cerevisiae*, wherein said strain is Taurus 07 with deposition number CBS128140.

4. A method of producing ethanol, the method comprising culturing the strain according to claim 1 in a culture comprising lignocellulosic material.

5. The method according to claim 4, wherein the culture further comprises a hydrolytic enzyme suitable for use in a simultaneous saccharification and fermentation (SSF) process.

6. A method of producing ethanol, the method comprising culturing the strain according to claim 2 in a culture comprising lignocellulosic material.

7. The method according to claim 6, wherein the culture further comprises a hydrolytic enzyme suitable for use in an SSF process.

8. A method of producing ethanol, the method comprising culturing the strain according to claim 3 in a culture comprising lignocellulosic material.

9. The method according to claim 8, wherein the culture further comprises a hydrolytic enzyme suitable for use in an SSF process.

* * * * *